(12) United States Patent
Higuchi

(10) Patent No.: US 7,366,331 B2
(45) Date of Patent: Apr. 29, 2008

(54) FINGERPRINT INPUT DEVICE

(75) Inventor: Teruyuki Higuchi, Tokyo (JP)

(73) Assignee: NEC Corporation, Tokyo (JP)

( * ) Notice: Subject to any disclaimer, the term of this patent is extended or adjusted under 35 U.S.C. 154(b) by 707 days.

(21) Appl. No.: 10/171,576

(22) Filed: Jun. 17, 2002

(65) Prior Publication Data
US 2003/0063783 A1    Apr. 3, 2003

(30) Foreign Application Priority Data
Jun. 18, 2001   (JP) .............................. 2001-183427

(51) Int. Cl.
*G06K 9/00*    (2006.01)
(52) U.S. Cl. .................... 382/124; 340/5.53; 340/5.83
(58) Field of Classification Search ........ 382/124–127; 250/556; 340/5.53, 5.83
See application file for complete search history.

(56) References Cited

U.S. PATENT DOCUMENTS

| | | | | |
|---|---|---|---|---|
| 5,446,290 A | * | 8/1995 | Fujieda et al. ............... | 250/556 |
| 5,942,761 A | * | 8/1999 | Tuli ........................... | 250/556 |
| 6,031,942 A | * | 2/2000 | Nakayama .................. | 382/284 |
| 6,259,108 B1 | * | 7/2001 | Antonelli et al. ............ | 250/556 |
| 6,292,576 B1 | * | 9/2001 | Brownlee .................... | 382/124 |
| 6,414,297 B1 | * | 7/2002 | Sasaki et al. ........... | 250/214 R |
| 2002/0097896 A1 | * | 7/2002 | Kuckendahl ................ | 382/124 |

FOREIGN PATENT DOCUMENTS

| | | |
|---|---|---|
| DE | 198 37 429 A1 | 8/1998 |
| JP | 63273976 | * 11/1988 |
| JP | 01-281583 | 11/1989 |
| JP | 02-170291 | 7/1990 |
| JP | 05-242229 | 9/1993 |
| JP | 06-325158 | 11/1994 |
| JP | 08-235361 | 9/1996 |
| JP | 9-116128 | 5/1997 |
| JP | 11-053524 | 2/1999 |

(Continued)

OTHER PUBLICATIONS

Japanese Office Action dated Feb. 22, 2005, with partial English translation.

(Continued)

*Primary Examiner*—Bhavesh M. Mehta
*Assistant Examiner*—John B Strege
(74) *Attorney, Agent, or Firm*—McGinn IP Law Group, PLLC

(57) ABSTRACT

A fingerprint input device capable of obtaining a fingerprint image presenting sufficient contrast is provided. The fingerprint input device includes: a two-dimensional image sensor for picking up a fingerprint image from a fingerprint measured portion of a measurement target finger; and a transparent solid film mounted on an image pickup surface of the two-dimensional image sensor, the fingerprint measured portion being mounted on the transparent solid film when the two-dimensional image sensor picks up the fingerprint image, wherein the fingerprint input device picks up an image of a fingerprint ridgeline portion in the fingerprint measured portion as a light portion, and picks up an image of a fingerprint valley portion in the fingerprint measured portion as a dark portion through an air layer, and a refractive index of the transparent solid film satisfies that contrast of the image is more than a given value.

42 Claims, 19 Drawing Sheets

FOREIGN PATENT DOCUMENTS

| | | |
|---|---|---|
| JP | 2000-076425 | 3/2000 |
| JP | 2000-217803 | 8/2000 |
| JP | 2001-092951 | 4/2001 |
| JP | 2001-119008 | 4/2001 |
| WO | WO 01/69520 A2 | 9/2001 |

OTHER PUBLICATIONS

Korean Office Action dated Aug. 30, 2004 with Japanese Translation and Partial English Translation.

European Search Report dated Jul. 26, 2005.

"CMOS Image Sensor with 1/7 Inch 110k Array and Color Processor", Fujitsu, System Solution LSI Division, Jun. 2001, pp. 1-2.

Taiwan Office Action dated Oct. 26, 2005 with a partial English translation.

English translation of the European Office Action dated Sep. 28, 2006.

* cited by examiner

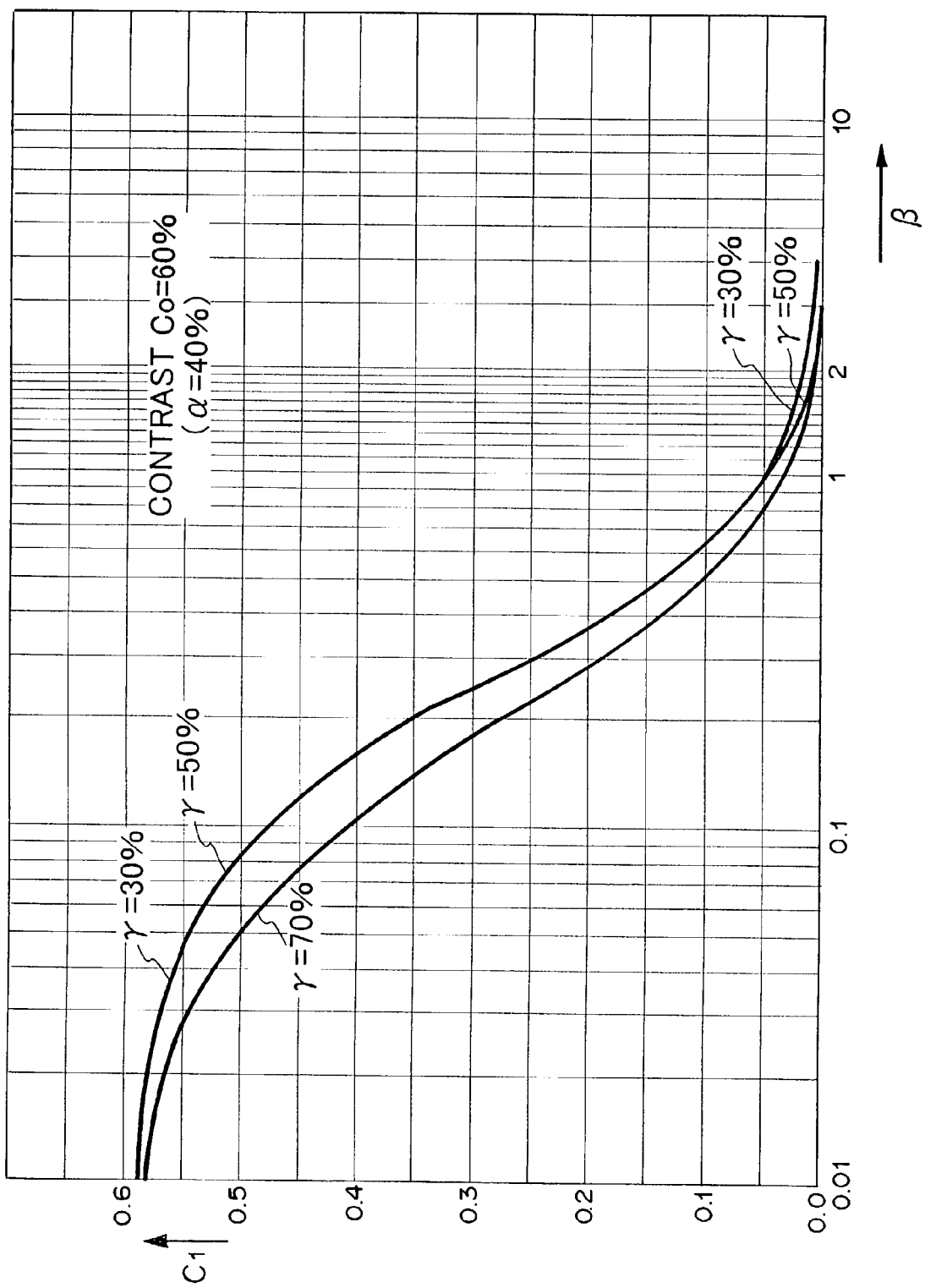

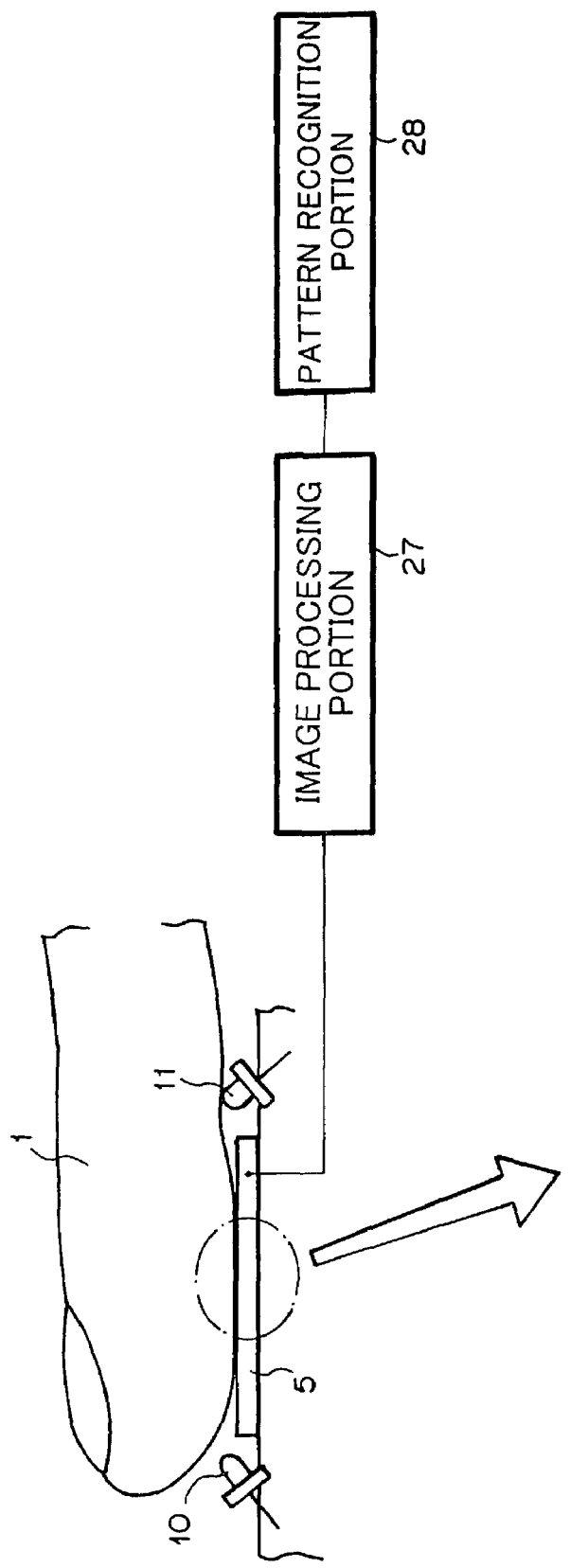

FINGERPRINT INPUT DEVICE

BACKGROUND OF THE INVENTION

1. Field of the Invention

The present invention relates to a fingerprint input device and particularly relates to a fingerprint input device for directly obtaining a fingerprint image using a two-dimensional image sensor.

2. Description of Related Art

Conventionally, a fingerprint input device of this type normally employs optical components such as a lens, a prism and an optical fiber, irradiates light to the fingerprint of a fingertip from a predetermined angle, converges light reflected by the fingerprint and outputs a fingerprint image. Further, a system of directly inputting a fingerprint image by electrostatic capacity instead of obtaining a fingerprint image using an optical system is studied.

A system of directly inputting a fingerprint image by an optical device is also studied. As the system, there are known a light reflection system for irradiating light to a fingertip skin and using reflected light therefrom and a light transmission system for inputting light into a finger and receiving the light emitted from the finger surface on the end face of an optical fiber flux.

According to these conventional fingerprint input devices, however, if optical components such as a lens, a prism or an optical fiber is employed, it is necessary to secure the magnitude of the optical components themselves, attachment locations therefor and the like to some extent. In addition, the optical components are relatively expensive, which disadvantageously prevents the fingerprint input device from being made thin and small in size and even prevents providing the device at low cost. Besides, if a fingerprint image is optically processed by the optical components, the obtained image disadvantageously tends to be distorted.

On the other hand, the system for directly inputting a fingerprint image by electrostatic capacity is disadvantageous in that the device is very weak to external static electricity and it is difficult to obtain good sensitivity.

Moreover, there is conventionally known an optical, reflection type fingerprint input device for directly obtaining a fingerprint image. According to this fingerprint input device, light is applied to a finger which faces the right surface of a two-dimensional image sensor from the rear surface of the sensor through the gap in the sensor. In a fingerprint ridgeline portion in which a film provided between the two-dimensional image sensor and the finger contacts the finger, the light applied to the finger enters the finger without being reflected by the contact surface. In a fingerprint valley portion in which the film is out of contact with the finger, the light not reflected by the film and the light emitted from the film is reflected by the surface of the finger and is incident again on the two-dimensional image sensor through the film. It is, therefore, possible to discriminate the fingerprint ridgeline portion from the fingerprint valley portion by whether or not the reflected light is incident on the two-dimensional image sensor. According to this device, it is necessary to apply light to the finger which faces the front surface of the two-dimensional image sensor, from the rear surface of the sensor. As a result, many portions which let light pass therethrough are required between sensor elements, which decreases the density of the sensor elements, sacrifices the resolution of the sensor, requires a special structure for the sensor, thereby pushing up manufacturing cost. Further, this device has an operational disadvantage in that if ambient light (disturbance light) enters the finger from a portion other than the measurement target surface of the finger, and is scattered in the finger, and passed through the contact surface between the fingerprint ridgeline portion and the film and incident on the optical image sensor, then the intensity of the incident light becomes almost equal to the reflected light and a fingerprint image cannot be obtained.

Furthermore, the conventionally known transmission type fingerprint input device utilizes a phenomenon that if a finger is pressed against the end face of an optical fiber flux and light is applied to the finger, then a fingerprint image appears. Due to this, it is required to use an intact and long optical fiber flux or a short slice of the optical fiber. As a result, the fingerprint input device becomes disadvantageously large in size or the manufacturing cost of the device is disadvantageously pushed up. In addition, there is a limit to making the optical fiber quite short, i.e., slicing the optical fiber to be thin, thereby disadvantageously restricting an attempt to make the device thin. Furthermore, the need of fingerprint input devices has widely spread to various fields. As a result, it become necessary to consider a case where a device is bent like an IC card, to attach the device to a curved surface such as a grip of various types, a writing tool or a shaft such as a pen-like pointer or the like. Therefore, it is insufficient to provide only a conventional two-dimensional image sensor which uses monocrystal silicon and which is not flexible at all.

The inventor of the present invention disclosed a fingerprint input device intended to solve these problems in Japanese Patent Application Laid-Open No. 2000-217803. This fingerprint input device is a light transmission type device, and does not include an optical fiber but a two-dimensional image sensor and a cover which is arranged on the two-dimensional image sensor, which is made of a transparent member such as glass and on which a fingertip is mounted. The fingerprint input device detects a fingerprint ridgeline portion in which the cover contacts a finger as a light portion and a fingerprint valley portion in which the cover is out of contact with the finger as a dark portion. This fingerprint input device may also include the first light source which irradiates light to the tip end of the fingertip and the second light source which irradiates light to the neighborhood of the first joint of the finger. The light emitted from these light sources enters the fingertip portion and scattered in the fingertip portion, and part of the scattered light is directed toward a fingerprint region. Therefore, it is possible to enhance the contrast of a fingerprint image detected by the two-dimensional image sensor.

However, Japanese Patent Application Laid-Open No. 2000-217803 only discloses that glass can be used as the cover employed in the fingerprint input device and does not specify the refractive index of the cover material and the thickness of the cover. As a result, depending on the refractive index of the cover material, a fingerprint image is not always sufficient in contrast. Further, depending on the thickness of the cover, a fingerprint image is not always sufficient in contrast and a protection function of protecting the two-dimensional image sensor is not always sufficient.

SUMMARY OF THE INVENTION

The present invention has been made in light of the above-stated problems. It is, therefore, an object of the present invention to provide a fingerprint input device capable of obtaining a fingerprint image presenting sufficient contrast.

It is another object of the present invention to provide a fingerprint input device having a sufficient protection function for protecting a two-dimensional image sensor.

It is yet another object of the present invention to provide a flexible fingerprint input device.

To attain the object of presenting sufficient contrast, the situations of the refraction, reflection and transmission of light between a finger and a transparent solid portion which contacts the finger have been analyzed in detail. As a result, the following matters have been found. In the fingerprint ridgeline portion, the reflection of light on the boundary surface between the finger and the transparent solid portion is almost zero and the light is transmitted into the transparent solid portion from the finger. In the fingerprint valley portion, an air layer is generated between the transparent solid portion and the finger skin. Due to this, the difference in refractive index between the interior of the finger and the air layer is great and the difference between the air layer and the transparent solid portion is great. As a result, in the fingerprint valley portion, reflectance is high on the two boundary surfaces and a reflection loss corresponding to the product of the two reflectances is generated when the scattered light from the finger is transmitted into the transparent solid film. In addition, a critical angle exists due to the relationship between the refractive index of the finger and that of the air when light is irradiated from the interior of the finger into the air. This is followed by the occurrence of a phenomenon that only about half the scattered light in the interior of the finger is emitted to the air. Though the present invention is of light transmission type, the structure of the present invention in which no optical fiber flux is used causes these advantageous phenomena and obtains a more reliable fingerprint ridgeline image, i.e., a ridgeline image with fewer missing parts than the conventional system which uses an optical fiber flux.

First, a film having such hardness that if a finger is put on the film, a fingerprint ridgeline portion is deformed to some extent and is closely appressed to the film and the film does not dig into a fingerprint valley portion is employed as a member which is in contact with the finger, i.e., a transparent solid film. This transparent solid film also should function as a protector for the surface of the two-dimensional image sensor, and it is necessary to select a film which is hard and strong However, this necessity does not contradict the above-stated conditions. Further, if a transparent solid film have a thickness sufficiently less than the distance between adjoining fingerprint ridgelines, a clear fingerprint image can be formed.

The refractive index of the transparent solid film will now be considered.

The finger cortex has a different refraction index depending on the dryness of a fingertip and individuals. However, the refractive index of water is 1.33, that of fat is 1.4 to 1.5 and that of wool which consists of animal protein is 1.56. Therefore, if it is estimated that the water content of the finger cortex is 40 to 50 wt %, the fat content thereof is 10 wt % and the protein content thereof is 50 to 40 wt %, then the refractive index of the finger cortex is in a range of 1.43 to 1.46, or if estimation error is considered, the refractive index of the finger cortex is in a range of 1.4 to 1.5.

According to the fingerprint input device disclosed in Japanese Patent Application Laid-Open No. 2000-217803, the material of the cover corresponding to the transparent solid film of the present invention is glass. The refractive index of the glass differs depending on the type of the glass as follows:

Quartz glass ($SiO_2$): 1.458
Pyrex glass ($Na_2O$—$B_2O_3$—$SiO_2$): 1.47
soda lime silica glass ($Na_2O$—$CaO$—$SiO_2$): 1.51 to 1.52
Dense flint glass: 1.6 to 1.7
$B_2O_3$ glass: 1.456
36BaO 64$B_2O_3$ glass: 1.630
5OPbO 5O$B_2O_3$ glass: 1.878
$GeO2$ glass: 1.607
$BeF_2$ glass: 1.2747
20LiF 30NaF 50$BeF_2$ glass: 1.315
25NaF 25$BaF_2$ 50$ZrF_4$ glass: 1.523
7LaF 33$ThF_4$ 60$ZrF_4$ glass: 1.547.

As can be seen, only in the above examples, the refraction index of the glass ranges from 1.2747 to 1.878. This range includes that of the refraction index of the finger and is wider than the latter.

Meanwhile, to obtain a binary image as a fingerprint image, contrast should be presented between the fingerprint ridgeline portion and the fingerprint valley portion. If the influence of noise due to disturbance light and noise generated in a circuits is considered, it is preferable that the contrast between the fingerprint ridgeline portion and the fingerprint valley portion is sharper. Therefore, the relationship between the refractive index of the transparent solid film and the contrast will now be considered using a model as shown in FIG. 1.

In FIG. 1, respective symbols indicate as follows:

①: a finger cortex portion
②: an air layer (reference numeral 7)
③: a transparent solid film (reference numeral 4)
n1: the refractive index of the finger cortex
n2: the refractive index of the air
n3: the refractive index of the transparent solid film
$\theta_{1L}$: the incidence angle of light on the transparent solid film right in the fingerprint ridgeline portion
$\theta_{3L}$: the outgoing angle of light to the transparent solid film right under the fingerprint ridgeline portion
$\theta_{1D}$: the incidence angle of light on the air layer in the fingerprint valley portion
$\theta_{2D}$: the outgoing angle of light to the air layer right under the fingerprint valley portion
$\theta_{2Di}$: the incidence angle of light on the transparent solid film from the air layer right under the fingerprint valley portion
$\theta_{3D}$: the outgoing angle of light on the transparent solid film from the air layer right under the fingerprint valley portion
$p_{1L}$: the power of light incident on the boundary between the interior of the finger cortex and the transparent solid film in the fingerprint ridgeline portion at angle $\theta_{1L}$ (since the light power is distributed uniformly in all directions in the finger cortex, $p_{1L}=p_1$, where $p_1$ is light power in the arbitrary direction in the finger cortex)
$p_{1D}$: the power of light incident on the boundary between the interior of the finger cortex and the air layer in the fingerprint valley portion with angle $\theta_{1D}$ ($p_{1D}=p_1$)
$p_{2D}$: the power of light emitted from the boundary between the interior of the finger cortex and the air layer in the fingerprint valley portion with angle $\theta_{2D}$
$p_{2Di}$: the incidence power of light directed toward the boundary between the air layer and the transparent solid film with angle $\theta_{2Di}$ among the light scattered in the air layer generated in the fingerprint valley portion
$p_{3L}$: the power of light emitted from the boundary between the finger cortex and the transparent solid film in the fingerprint ridgeline portion with angle $\theta_{3L}$
$p_{3D}$: the power of light emitted from the boundary between the air layer and the transparent solid film in the fingerprint valley portion with angle $\theta_{3D}$.

Contrast $C_0$ before contrast reduction occurs due to the thickness of the transparent solid film is defined as follows:

$$C_0 = (P_{3L} - P_{3D})/P_{3L} \qquad (1)$$
$$= (P_{3L}/P_1 - P_{3D}/P_1)/P_{3L}/P_1$$
$$= \left(T_{L(①→③)} - T_{D(①→②→③)}\right) / T_{L(①→③)}$$

where $P_{3D}$: the power of downward light in all directions right under the fingerprint valley portion, $P_{3L}$: the power of downward light in all directions right under the fingerprint ridgeline portion, $P_1$: the power of downward light existing in the finger cortex portion, $T_D(①→②→③)$: the transmittance of light in all directions transmitted to the region right under the fingerprint valley portion (transmittance for light emitted from the finger cortex portion ① to the air layer ②, scattered in the air layer ② and incident on the transparent solid film ③, and $T_L(①→③)$: the transmittance of light in all directions transmitted to the region right under the fingerprint ridgeline portion (the transmittance of light directly incident on the transparent solid film ③ from the finger cortex portion ①).

Here, refractive index conditions involve two conditions, i.e., the first refractive index condition: $n_3 \geq n_1 > n_2 = 1.000$ and the second refractive index condition: $n_1 > n_3 > n_2 = 1.000$.

Under the first refractive index condition, the following equation is satisfied for the fingerprint valley portion:

$$\text{Valley portion: } P_{3D} = \left(p_1 \int_0^{\theta_c} t_D(①→②) d\theta\right) \cdot \left(\int_0^{90°} t_D(②→③) d\theta\right) \qquad (2)$$

Under the first refractive index condition, the following equation is satisfied for the fingerprint ridgeline portion:

$$\text{Ridgeline portion: } P_{3L} = \left(p_1 \int_0^{90°} t_L(①→③) d\theta\right) \qquad (3)$$

In the equations, $t_D$: the transmittance of light for each incidence angle in the valley portion, and $t_L$: the transmittance of light for each incidence angle in the ridgeline portion.

Under the second refractive index condition, the following equation is satisfied for the fingerprint valley portion as in the case of the first refractive index condition:

$$\text{Valley portion: } P_{3D} = \left(p_1 \int_0^{\theta_c} t_D(①→②) d\theta\right) \cdot \left(\int_0^{90°} t_D(②→③) d\theta\right) \qquad (2)$$

Under the second rdfractive index condition, the following equation is satisfied for the ridgeline portion:

Ridgeline portion:

$$\text{Ridgeline portion: } P_{3L} = \left(p_1 \int_0^{\theta_c(①→③)} t_D(①→③) d\theta\right) \qquad (4)$$

Transmittances $t_D$ and $t_L$ are the average transmittances of the components P and S of the light power, respectively. That is, $t_D$ and $t_L$ are expressed as follows:

$$t_D(t_{PD}+t_{SD})/2 \qquad (5), \text{ and}$$

$$t_L=(t_{PL}+t_{SL})/2 \qquad (6).$$

Here, the general equation of tp is expressed as follows:

$$t_P=(\sin 2\theta_i \cdot \sin 2\theta_o)/(\sin^2(\theta_i+\theta_o) \cdot \cos(\theta_i-\theta_o)) \qquad (7)$$

The general equation of $t_S$ is expressed as follows:

$$t_S=(\sin 2\theta_i \cdot \sin 2\theta_o)/\sin^2(\theta_i+\theta_o) \qquad (8)$$

Therefore, the general equation of average transmittance t is expressed as follows:

$$t=(½) \cdot (\sin 2\theta_i \cdot \sin 2\theta_o)/\sin^2(\theta_i+\theta_o) \, (1+1/\cos(\theta_i-\theta_o)) \qquad (9)$$

In these equation, $$\theta_o = \sin^{-1}(n_1/n_0 \sin \theta_1) \qquad (10)$$

where $\theta_i$: incidence angle $\theta_o$: outgoing angle $n_1$: incidence light-side refractive index $n_o$: outgoing light-side refractive index.

$\theta_O$ is univocally determined by $\theta_i$.

From the equation (10), the following equation is satisfied:

$$n_o \sin \theta_o = n_1 \sin \theta_1 \qquad (10').$$

In addition, when $n_1 > n_o$, a critical angle $\theta_c$ is obtained by the following equation:

$$\theta_c = \sin^{-1}(n_o/n_1).$$

From the above, under the first refractive index condition, the following equations are satisfied for the fingerprint valley portion:

$$P_{3D} = \left(|p_1| \cdot \int_0^{\theta_c(①→②)} t_D(①→②) d\theta_{1D}\right) \cdot \left(\int_0^{90°} t_D(②→③) d\theta_{2Di}\right) \qquad (12)$$

where $$\theta_{C(①→②)} = \sin^{-1}(n_2/n_1) \qquad (13)$$

$$t_{D(①→②)} = (½) \cdot (\sin 2\theta_{1D} \cdot \sin 2\theta_{2D})/\sin^2(\theta_{1D}+\theta_{2D}) \cdot (1+1/\cos(\theta_{1D}-\theta_{2D})) \qquad (14)$$

$$\theta_{2D} = \sin^{-1}(n_1/n_2 \sin \theta_{1D}) \qquad (15)$$

$$t_{D(②→③)} = (½) \cdot (\sin 2\theta_{2Di} \cdot \sin 2\theta_{3D})/\sin^2(\theta_{2Di}+\theta_{3D}) \cdot (1+1/\cos(\theta_{2Di}-\theta_{3D})) \qquad (16)$$

$$\theta_{3D} = \sin^{-1}(n_2/n_3 \sin \theta_{2Di}) \qquad (17)$$

$\theta_{1D}$: the incidence angle of light incident on the air layer in the fingerprint valley portion $\theta_{2Di}$: the incidence angle of light incident on the transparent solid film from the air layer right under the fingerprint valley portion In addition, under the first refractive index condition, the following equations are satisfied for the fingerprint ridgeline portion:

$$P_{3L} = \left( |p_1| \cdot \int_0^{90°} t_L(\text{①} \to \text{③}) d\theta_{1D} \right) \quad (18)$$

where $t_L(\text{①} \to \text{③}) = (\frac{1}{2}) \cdot (\sin 2\theta_{1L} \cdot \sin 2\theta_{3L})/\sin^2(\theta_{1L}+\theta_{3L}) \cdot (1+1/\cos(\theta_{1L}-\theta_{3L}))$ (19)

$\theta_{3L} = \sin^{-1}(n_1/n_3 \sin \theta_{1L})$ (20)

$\theta_{1L}$: the incidence angle of light incident on the transparent solid film in the fingerprint ridgeline portion Under the second refractive index condition as in the case of the first refractive index condition, the following equations are satisfied for the fingerprint valley portion:

$$P_{3D} = \left( |p_1| \cdot \int_0^{\theta_c(\text{①} \to \text{②})} t_D(\text{①} \to \text{②}) d\theta_{1D} \right) \cdot \left( \int_0^{90°} t_D(\text{②} \to \text{③}) d\theta_{2Di} \right) \quad (12)$$

where $\theta_{C(\text{①} \to \text{②})} = \sin^{-1}(n_2/n_1)$ (13)

$t_{D(\text{①} \to \text{②})} = (\frac{1}{2}) \cdot (\sin 2\theta_{1D} \cdot \sin 2\theta_{2D})/\sin^2(\theta_{1D}+\theta_{2D}) \cdot (1+1/\cos(\theta_{1D}-\theta_{2D}))$ (14)

$\theta_{2D} = \sin^{-1}(n_1/n_2 \sin \theta_{1D})$ (15)

$t_{D(\text{②} \to \text{③})} = (\frac{1}{2}) \cdot (\sin 2\theta_{2Di} \cdot \sin 2\theta_{3D})/\sin^2(\theta_{2Di}+\theta_{3D}) \cdot (1+1/\cos(\theta_{2Di}-\theta_{3D}))$ (16)

$\theta_{3D} = \sin^{-1}(n_2/n_3 \sin \theta_{2Di})$ (17)

$\theta_{1D}$: the incidence angle of light incident on the air layer in the fingerprint valley portion $\theta_{2Di}$: the incidence angle of light incident on the transparent solid film from the air layer right under the fingerprint valley portion In addition, under the second refractive index condition, the following equations are satisfied for the fingerprint ridgeline portion:

$$P_{3L} = \left( |p_1| \cdot \int_0^{\theta_c(\text{①} \to \text{③})} t_L(\text{①} \to \text{③}) d\theta_{1D} \right) \quad (21)$$

where $\theta_{C(\text{①} \to \text{③})} = \sin^{-1}(n_3/n_1)$ (22)

$t_{L(\text{①} \to \text{③})} = (\frac{1}{2}) \cdot (\sin 2\theta_{1L} \cdot \sin 2\theta_{3L})/\sin^2(\theta_{1L}+\theta_{3L})/\sin^2(\theta_{1L}-\theta_{3L}))$ (23)

$\theta_{3L} = \sin^{-1}(n_1/n_3 \sin \theta_{1L})$ (24)

Accordingly, under the first refractive index condition, the contrast $C_0$ is obtained by assigning the equations (12) and (18) to the equation (1). Under the second refractive index condition, the contrast $C_0$ is obtained by assigning the equations (12) and (21) to the equation (1).

Next, a contrast calculation result using the above-stated equations will be described. FIGS. 2 and 3 are graphs each showing the relationship between the refractive index of the transparent solid film and the contrast calculated using the above equations. For the convenience of the formation of graphs, the refractive index range of the transparent solid film is from 1.0 to 2.0 in FIG. 2 and that is from 1.0 to 5.0 in FIG. 3. A line obtained by connecting points "+" indicates a case where the refractive index of the finger cortex is 1.4. A line obtained by connecting points "x" indicates a case where the refractive index of the finger cortex is 1.5. FIGS. 2 and 3 show the following. If the refractive index of the transparent solid film is 1.0, the contrast $C_0$ is 0%. As the refractive index of the transparent solid film increases until it equals that of the finger cortex, the contrast $C_0$ increases up to the maximum. As the refractive index of the transparent solid film further increases from that of the finger cortex, the contrast $C_0$ slightly decreases once and then slightly increases. The maximum of the contrast $C_0$ is about 63% if the refractive index of the finger cortex is 1.4 and about 58% if the refractive index of the finger cortex is 1.5.

In addition, FIG. 2 shows the following. If the refractive index of the transparent solid film is 1.4 and that of the finger cortex is 1.4, then the contrast $C_0$ is about 60%. If the refractive index of the transparent solid film is 1.4 and that of the finger cortex is 1.5, then the contrast $C_0$ is as low as about 50%. On the other hand, if the refractive index of the transparent solid film is 1.5 and that of the finger cortex is 1.4, then the contrast $C_0$ is about 58%. If the refractive index of the transparent solid film is 1.5 and that of the finger cortex is 1.5, then the contrast $C_0$ is about 63%. This, therefore, indicate that if the difference in the refractive index of the finger cortex among individuals, the fluctuation of the refractive index because of the humidity of the finger and the other dispersion factors are considered, the refractive index of the transparent solid film is preferably not less than the maximum refractive index of the finger cortex. As the maximum value, 1.5, for example, is selected as stated above.

It is noted that the contrast $C_0$ is not always needed to be set at the maximum. If a desired contrast is given, the refractive index of the transparent solid film may be set so that the contrast $C_0$ determined by the refractive index of the transparent solid film becomes not less than the desired contrast (e.g., 50%). Under the first refractive index condition, the contrast $C_0$ determined by the refractive index of the transparent solid film is obtained by assigning the equations (12) and (18) to the equation (1). Under the second refractive index condition, the contrast $C_0$ determined by the refractive index of the transparent solid film is obtained by assigning the equations (12) and (21) to the equation (1). By setting the contrast $C_0$ in this way, it is possible to specify the lower limit of the refractive index of the transparent solid film. On the other hand, even if the refractive index of the transparent solid film increases, the contrast tends to hardly decrease but rather increase. Therefore, the upper limit of the refractive index of the transparent solid film cannot be specified by the desired contrast $C_0$. In other words, to obtain the desired contrast $C_0$, it is sufficient that the refractive index is not less than a certain value and no restriction is given to the upper limit of the refractive index. If the desired contrast $C_0$ is, for example, 40%, the lower limit of the refractive index can be specified to about 1.3 but the upper limit thereof cannot be specified.

FIGS. 4 to 7 are graphs each showing the relationship between the refractive index of the transparent solid film and the transmittance obtained in the process of obtaining the graphs of refractive index verses contrast. FIGS. 4 and 5 are graphs in the case of the refractive index of the finger is 1.4, and FIGS. 6 and 7 are graphs in the case of the refractive index of the finger is 1.5. For the convenience of the formation of the graphs, the refractive index range of the transparent solid film is from 1.0 to 2.0 in FIGS. 4 and 6 and that is from 1.0 to 5.0 in FIGS. 5 and 7. A line obtained by connecting points "*" indicates the transmittance $T_L(①→③))$ of light in all directions transmitted to the region right under the fingerprint ridgeline portion in the fingerprint ridgeline portion. A line obtained by connecting points "+" indicates the transmittance $T_D(①→②→③)$ of light in all directions transmitted to the region right under the fingerprint valley portion in the fingerprint ridgeline portion. FIGS. 4 to 7 show the following. The transmittance $T_L(①→③)$ of the light in all directions transmitted to the region right under the fingerprint ridgeline portion in the fingerprint ridgeline portion increases until the refractive index of the transparent solid film increases from 1.00 to be equal to that of the finger. The transmittance $T_L(①→③)$ decreases as the refractive index of the transparent solid film further increases from that of the finger. Further, the transmittance $T_D(①→②→③)$ of the light in all directions toward the region right under the fingerprint valley portion in the fingerprint ridgeline portion monotonously decreases as the refractive index of the transparent solid film increases from 1.00.

FIGS. 2 and 3 show that the contrast $C_0$ has little change as long as the refractive index of the transparent solid film is not less than that of the finger cortex. FIGS. 4 to 7 show that the transmittance of light in the fingerprint ridgeline portion and that in the fingerprint valley portion decrease as the refractive index of the transparent solid film increases in a range in which the refractive index of the transparent solid film is not less than that of the finger cortex. Therefore, when the refractive index of the transparent solid film is high, then lightness decreases, an S/N ratio (signal-to-noise ratio) decreases, where the level of noise due to disturbance light and that generated in the circuits is assumed as a noise component, and the possibility that the discrimination of the fingerprint ridgeline portion from the fingerprint valley portion becomes inaccurate even if the contrast is presented. As a result, the upper limit of the refractive index of the transparent solid film is required to be specified so that the S/N ratio, on the assumption of noise of a predetermined value, becomes not less than a desired value. If the intensity of light irradiated to the finger is increased, the lightness (signal component) of the fingerprint ridgeline portion and that of the fingerprint valley portion detected by the two-dimensional image sensor increase. At the same time, however, the lightness (noise component) of the disturbance light reflected by the surface of the finger cortex increases. As a result, the S/N ratio cannot be increased by increasing the intensity of the light irradiated to the finger. This means that the S/N ratio should be limited to be not less than a predetermined value by restricting the upper limit of the refractive index of the transparent solid film. As the desired value of the S/N ratio, 10 dB or 20 dB is selected, for example.

It is noted, however, that it is unnecessary to strictly restrict the upper limit because the decrease of the lightness (signal component) of the fingerprint ridgeline portion and that of the fingerprint valley portion which are detected by the two-dimensional image sensor as a result of the increase of the refractive index of the transparent solid film are small. If the refractive index of the finger cortex is 1.4, the refractive index of the film verses the transmittance is obtained as shown in Table 1 below.

|  | $n_3 = 1.4$ | $n_3 = 2.0$ | $n_3 = 3.0$ | $n_3 = 4.0$ | $n_3 = 5.0$ |
| --- | --- | --- | --- | --- | --- |
| Ridgeline portion | 1.022 (100%) | 0.875 (86%) | 0.785 (77%) | 0.709 (69%) | 0.648 (63%) |
| Valley portion | 0.411 (100%) | 0.375 (91%) | 0.325 (79%) | 0.288 (70%) | 0.259 (63%) |

In addition, if the refractive index of the finger cortex is 1.5, the relationship where the refractive index of the film verses the transmittance is obtained as shown in Table 2 below.

|  | $n_3 = 1.5$ | $n_3 = 2.0$ | $n_3 = 3.0$ | $n_3 = 4.0$ | $n_3 = 5.0$ |
| --- | --- | --- | --- | --- | --- |
| Ridgeline portion | 1.022 (100%) | 0.890 (87%) | 0.800 (78%) | 0.731 (72%) | 0.667 (65%) |
| Valley portion | 0.406 (100%) | 0.375 (92%) | 0.325 (80%) | 0.288 (71%) | 0.259 (64%) |

The tables 1 and 2 show the following. If the refractive index of the transparent solid film becomes 2.0, the transmittance decreases by ten-odd percent. If the refractive index of the transparent solid film becomes 3.0, the transmittance decreases by about 20%. If the refractive index of the transparent solid film becomes 4.0, the transmittance decreases by about 30%. If the refractive index of the transparent solid film becomes 5.0, the transmittance decreases by about 35%. Accordingly, if the decrease rate of the transmittance should be suppressed to about ten-odd percent, then the refractive index of the transparent solid film should be set at 2.0 or less. If the decrease rate of the transmittance should be suppressed to about 20%, then the refractive index of the transparent solid film should be set at 3.0 or less. If the decrease rate of the transmittance should be suppressed to about 30%, the refractive index of the transparent solid film should be set at 4.0 or less. If the decrease rate of the transmittance should to be suppressed to about 35%, the refractive index of the transparent solid film should be set at 5.0 or less.

If the thickness of the transparent solid film is far less than the distance between adjoining fingerprint ridgelines, contrast $C_1$ detected by the two-dimensional image sensor is equal to the contrast $C_0$ expressed by the equation (1). Otherwise, the contrast $C_1$ detected by the two-dimensional image sensor is lower than the contrast $C_0$ expressed by the equation (1) because of the contrast decrease due to the thickness of the transparent solid film. We now consider a condition that the contrast $C_1$ which is detected by a certain two-dimensional image sensor is not less than a desired contrast $C_{1D}$. The lower limit of the refractive index of the transparent solid film is therefore in question so that the contrast $C_0$ obtained by assigning the equations (12) and (18) or the equations (12) or (21) to the equation (1) satisfies this condition. Such a lower limit is the refractive index of the transparent solid film which satisfies that contrast $C_0$ becomes $C_{1D}$ only under the condition that the thickness of the transparent solid film is almost zero. Therefore, if the contrast $C_{1D}$ which should detected by a certain two-dimensional image sensor is given, the contrast $C_{1D}$ must be compensated for reduction due to a certain thickness of the transparent solid film in order to specify the lower limit of the refractive index of such a transparent solid film of the thickness. Therefore, the refractive index of the transparent solid film is determined by not only a desired contrast $C_{1D}$ but also the thickness of the transparent solid film. However, if the thickness of the transparent solid film is set in advance, the refractive index of the transparent solid film is determined only by a desired contrast which has been compensated for the reduction due to the thickness.

Nevertheless, as described above, the maximum contrast $C_0$ is obtained if the refractive index of the transparent solid film is not less than the maximum refractive index of the finger cortex in consideration of the dispersion of the refractive index of the finger cortex. As long as the refractive index is not extremely high, the transmittance does not decrease. Therefore, it is allowed to determine the thickness of the transparent solid film after setting the refractive index of the transparent solid film at the maximum refractive index of the finger cortex in consideration of the dispersion of the refractive index of the finger cortex.

Next, the thickness of the transparent solid film will be considered.

FIG. 8 is a typical view showing light received at a point $X_0$ right under the central point of the fingerprint ridgeline portion. In FIG. 8, symbol "w" denotes the distance between fingerprint ridgelines, "t" denotes the thickness of the transparent solid film, $P_{3L}$ denotes the intensity of light emitted from the fingerprint ridgeline portion (=the power of downward light in all directions right under the fingerprint ridgeline portion), $P_{3D}(=\alpha P_{3L})$ denotes the intensity of light emitted from the fingerprint valley portion (=the power of downward light in all directions right under the fingerprint valley portion), and γ denotes the duty of the fingerprint ridgeline portion. Because the fingerprint ridgeline portion can be discriminated from the fingerprint valley portion, it is possible to make an assumption that the light received at the point $X_0$ are the light $A_{-1}$ from a half of the fingerprint valley portion adjacent to the finger print ridgeline portion right over the point $X_0$, the light $A_0$ from the fingerprint ridgeline portion right over the point $X_0$ and the light $A_1$ from a half of the other fingerprint valley portion adjacent to the fingerprint ridgeline portion right over the point $X_0$ The sum $I_{x0}$ of the light received at the point $X_0$ is expressed as follows.

$$I_{X0} = A_{-1} + A_0 + A_1 \qquad (24)$$

$$= P_{3D}\int_{-w/2}^{-\gamma w/2}\frac{dx}{t^2+x^2} + P_{3L}\int_{-\gamma w/2}^{\gamma w/2}\frac{dx}{t^2+x^2} +$$

$$P_{3D}\int_{\gamma w/2}^{w/2}\frac{dx}{t^2+x^2}$$

$$= \frac{2P_{3L}}{t}\left(\tan^{-1}\frac{\gamma}{2\beta} + \alpha\tan^{-1}\frac{1}{2\beta} - \alpha\tan^{-1}\frac{\gamma}{2\beta}\right)$$

where $$\beta=t/w.$$

FIG. 9 is a typical view showing light received at a point $X_1$ right under the central point of the fingerprint valley portion. In FIG. 9, symbol "w" denotes the distance between fingerprint ridgelines, "t" denotes the thickness of the transparent solid film, $P_{3L}$ denotes the intensity of light emitted from the fingerprint ridgeline portion, $P_{3D}$ (=$\alpha P_{3L}$) denotes the intensity of light emitted from the fingerprint valley portion, and "γ" denotes the duty of the fingerprint ridgeline portion. It is possible to make an assumption that the light received at the point $X_1$ are the light $B_{-1}$ from a half of the fingerprint ridgeline portion adjacent to the fingerprint valley portion right over the point $X_1$, the light $B_0$ from the fingerprint valley portion right over the point $X_1$ and the light $B_1$ from a half of the other fingerprint ridgeline portion adjacent to the fingerprint valley portion right over the point $X_1$. The sum $I_{X1}$ of the light received at the point $X_1$ is expressed as follows.

$$I_{X0} = B_{-1} + B_0 + B_1 \qquad (25)$$

$$= P_{3L}\int_{-w/2}^{-(1-\gamma)w/2}\frac{dx}{t^2+x^2} + P_{3D}\int_{-(1-\gamma)w/2}^{(1-\gamma)w/2}\frac{dx}{t^2+x^2} +$$

$$P_{3L}\int_{(1-\gamma)w/2}^{w/2}\frac{dx}{t^2+x^2}$$

$$= \frac{2P_{3L}}{t}\left(\alpha\tan^{-1}\frac{1-\gamma}{2\beta} + \tan^{-1}\frac{1}{2\beta} - \tan^{-1}\frac{\gamma}{2\beta}\right)$$

where, β=t/w.

Accordingly, the contrast $C_1$ is expressed as follows:

$$C_1 = 1 - \frac{I_{X1}}{I_{X0}} \qquad (26)$$

$$= 1 - \frac{\alpha\tan^{-1}\frac{1-\gamma}{2\beta} + \tan^{-1}\frac{1}{2\beta} - \tan^{-1}\frac{\gamma}{2\beta}}{\tan^{-1}\frac{\gamma}{2\beta} + \alpha\tan^{-1}\frac{1}{2\beta} - \alpha\tan^{-1}\frac{\gamma}{2\beta}}$$

$$= 1 - \frac{(1-C_0)\tan^{-1}\frac{1-\gamma}{2\beta} + \tan^{-1}\frac{1}{2\beta} - \tan^{-1}\frac{\gamma}{2\beta}}{\tan^{-1}\frac{\gamma}{2\beta} + (1-C_0)\tan^{-1}\frac{1}{2\beta} - (1-C_0)\tan^{-1}\frac{\gamma}{2\beta}}$$

FIG. 10 is a graph showing the relationship between the ratio β of the thickness of the transparent solid film to the distance of the fingerprint ridgelines and the contrast $C_1$ in case of the contrast $C_0$ is 100%, i.e., α=0%. In FIG. 10, three curves show cases where the duties γ of the fingerprint ridgeline portion are 30%, 50% and 70%, respectively.

As calculated from the equation (26), in the case of $C_0$=100%, the value of β which satisfies that the contrast $C_1$ is 10% and 20% with respect to the duties γ of 30%, 50% and 70% are shown in the following table.

|  | γ | | |
| --- | --- | --- | --- |
| $C_1$ | 30% | 50% | 70% |
| 10% | 1.25 | 1.04 | 0.78 |
| 20% | 0.82 | 0.68 | 0.48 |

Likewise, FIG. 11 is a graph showing the relationship between the ratio β of the thickness of the transparent solid film to the distance of the fingerprint ridgelines and the contrast $C_1$ in case of the contrast $C_0$=60%, i.e., α=40%. In FIG. 11, three curves show cases where the duties γ of the fingerprint ridgeline portion are 30%, 50% and 70%, respectively. As is obvious from the above consideration about the refractive index of the transparent solid film, the contrast $C_0$ becomes 60% when the refractive index of the transparent solid film is approximately equal to that of the finger cortex and close to an optimum value.

As calculated from the equation (26), in the case of $C_0=60\%$, the value of $\beta$ which satisfied that the contrast $C_1$ is 10% and 20% with respect to the duties $\gamma$ of 30%, 50% and 70% are shown in the following table.

|  | γ | | |
| --- | --- | --- | --- |
| $C_1$ | 30% | 50% | 70% |
| 10% | 0.64 | 0.64 | 0.51 |
| 20% | 0.38 | 0.39 | 0.29 |

Accordingly, if the duty of the fingerprint ridgeline portion is from 30% to 50%, the refractive index of the transparent solid film is approximately equal to that of the finger cortex and the contrast $C_0$ is a maximum of 60%, then the ratio $\beta$ of the thickness of the transparent solid film to the distance between the fingerprint ridgelines should be 0.64 or less so as to obtain the contrast $C_1$ of 10%. Since the minimum distance between the fingerprint ridgelines is approximately 100 μm, the thickness of the transparent solid film should be 64 μm or less.

Further, if the duty of the fingerprint ridgeline portion is 70%, the refractive index of the transparent solid film is approximately equal to that of the finger cortex and the contrast $C_0$ is a maximum of 60%, then the ratio $\beta$ of the thickness of the transparent solid film to the distance between the fingerprint ridgelines should be 0.51 or less so as to obtain the contrast $C_1$ of 10%. Since the minimum distance between the fingerprint ridgelines is approximately 100 μm, the thickness of the transparent solid film should be 51 μm or less.

Likewise, if the duty of the fingerprint ridgeline portion is 30%, the refractive index of the transparent solid film is approximately equal to that of the finger cortex and the contrast $C_0$ is a maximum of 60%, then the ratio $\beta$ of the thickness of the transparent solid film to the distance between the fingerprint ridgelines should be 0.38 or less so as to obtain the contrast $C_1$ of 20%. Since the minimum distance between the fingerprint ridgelines is approximately 100 μm, the thickness of the transparent solid film should be 38 μm or less.

Furthermore, if the duty of the fingerprint ridgeline portion is 50%, the refractive index of the transparent solid film is approximately equal to that of the finger cortex and the contrast $C_0$ is a maximum of 60%, then the ratio $\beta$ of the thickness of the transparent solid film to the distance between the fingerprint ridgelines should be 0.39 or less so as to obtain the contrast $C_1$ of 20%. Since the minimum distance between the fingerprint ridgelines is approximately 100 μm, the thickness of the transparent solid film should be 39 μm or less.

In addition, if the duty of the fingerprint ridgeline portion is 70%, the refractive index of the transparent solid film is approximately equal to that of the finger cortex and the contrast $C_0$ is a maximum of 60%, then the ratio $\beta$ of the thickness of the transparent solid film to the distance between the fingerprint ridgelines should be 0.29 or less so as to obtain the contrast $C_1$ of 20%. Since the minimum distance between the fingerprint ridgelines is approximately 100 μm, the thickness of the transparent solid film should be 29 μm or less.

Consequently, considering that the finger can be detected from the output of the fingerprint input device if the contrast $C_1$ is about 10%, the duty of the fingerprint ridgeline portion is typically 50% and that the minimum distance between the fingerprint ridgelines is approximately 100 μm, it follows that the thickness of the transparent solid film should be 64 μm or less.

Meanwhile, while the transparent solid film functions to protect the two-dimensional image sensor, it is difficult that the transparent solid film has complete wear resistance and may possibly be damaged. It is, therefore, preferable that the transparent solid film has a thickness to at least such an extent that the film is not pierced with holes even if the film is worn and damaged after the film has been used many times for a long period of time. While depending on the hardness of the transparent solid film, this thickness may be a finite thickness exceeding zero.

Furthermore, since this transparent solid film also functions as a protection film, the durability of the film is higher as the transparent solid film is thicker if the film is used in a location exposed to the weather. However, if the thickness of the transparent solid film increases, the contrast between the fingerprint ridgeline portion and the fingerprint valley portion cannot be presented as already stated above. To ensure both durability and contrast, therefore, the transparent solid film may be partitioned by small cell-like light shielding walls each formed out of a light shielding material and then the transparent solid film may be made thick to shield light having a horizontal velocity component. Such a film is obtained by piercing penetrating holes in a shielding film having a desired thickness so that the penetrating holes are sufficiently smaller in size than the sensor elements and the distance between the elements and are aligned at the highest density, filling a transparent solid material into the penetrating holes in the light shielding film and flattening the surface of the film to have sufficiently smaller irregularities than those of the fingerprint. The film thus obtained is closely attached to the surface of the photosensitive portion of the two-dimensional image sensor. In this case, the thickness of the film is intended to be as large as the distance between the fingerprint ridgelines upon setting the diameter of each penetrating hole smaller than the distance between the fingerprint ridgelines. As a result, the penetrating holes are longwise penetrating holes, which require advanced manufacturing technique. However, if the latest semiconductor manufacturing technology is utilized, the device can be easily manufactured.

Furthermore, the cell-like light shielding walls may be formed so as to be aligned to each element of the two-dimensional image sensor. By doing so, it is possible to set the size of each penetrating hole to be as large as that of one element. In this case, the utilization rate of the light incident on the transparent solid film can be increased and the ratio of the height and diameter of each penetrating hole can be set lower than in a case where such alignment is not made, thereby facilitating manufacture of the device. In that case, however, it is also necessary that the positions of all penetrating holes are consistent with those of the respective elements of the two-dimensional image sensor. As a result, it is difficult to separately manufacture the transparent solid film and the two-dimensional image sensor and then to attach them to each other. Considering this, it is necessary to manufacture the transparent solid film by a part of the method of manufacturing the two-dimensional sensor. Since it is unnecessary to provide a special purpose two-dimensional image sensor but the image sensor may be a standard one, it is sufficient to add a process of providing the transparent protection film to a final process in the method of manufacturing the standard two-dimensional image sensor. Therefore, no special manufacturing method is required and manufacturing cost is not excessively pushed up.

There is an adverse effect of the electrostatic breakdown of the two-dimensional image sensor and the like due to static electricity generated at the fingertip, though it is less than that of the electrostatic capacity type fingerprint input device. To lessen the fear of the electrostatic breakdown of the two-dimensional image sensor, an electrical conductive material, e.g., metal, is used as the light shielding material for forming the above-stated cell-like light shielding walls and the walls are grounded so that the static electricity can be relieved. Further, even if the simple transparent solid film stated initially is employed, the static electricity generated on the fingertip can be relieved by attaching an electrical conductive transparent film to the surface of the transparent solid film and grounding the electrical conductive transparent film. As the material of the electrical conductive transparent film, tin oxide or ITO (Indium-tin oxide), for example, is available. It is desirable that the electrical conductive transparent film has a refractive index higher than that of the finger and not higher than that of the transparent solid film. However, since the refractive index of a transparent material containing metal oxide such as indium oxide having large atomic weight is higher than 1.5 and therefore satisfies the former condition, the both conditions can be satisfied by appropriately selecting the refractive index of the transparent solid film having the refractive index to satisfy the latter condition.

According to the light transmission type fingerprint input device, disturbance light irradiated to the surface of the finger except for a fingerprint measured portion (a portion having a fingerprint) acts as a kind of a light source and does not adversely influence the input of the fingerprint. However, abnormally strong disturbance light or disturbance light applied to a part of the photosensitive portion of the two-dimensional image sensor whose part is not closed by the finger is undesirable. Considering this, by closely attaching an infrared filter to the photosensitive portion of the two-dimensional image sensor and using an infrared ray as light to be irradiated to the finger, almost all normal disturbance light to be incident on the photosensitive portion can be shielded and a stable fingerprint image less influenced by the disturbance light can be thereby obtained. The infrared filter film, which is normally thin, is bonded to the surface of the transparent solid film or bonded onto the cover film of the two-dimensional image sensor (whose cover film is provided to stabilize the characteristic of the elements, should be formed in a semiconductor manufacturing process and is, therefore, normally as very thin as several micrometers or less due to a semiconductor device manufacturing method). An infrared ray emission LED is employed as the light source of infrared rays. If the infrared filter film is bonded to the surface of the transparent solid film, the filter film desirably has a refractive index not lower than that of the finger and not higher than that of the transparent solid film. In addition, if the infrared filter film is bonded onto the cover film, the film desirably has a refractive index not lower than that of the transparent solid film and not higher than that of the cover film. It is also possible that the interior of the transparent solid film functions as an infrared filter film.

If an infrared ray is used, it follows that the transparent solid film is transparent means that it is transparent for an infrared waveband irrespectively of a method of realizing the infrared filter.

Alternatively, the infrared filter may be used together with the above-stated electrical conductive transparent film. In this case, the electrical conductive transparent film is provided as the uppermost layer so as to contact the fingerprint measured portion of the finger.

In addition, a two-dimensional image sensor constituted so that a convex lens is mounted right over the respective light receiving elements of a two-dimensional image sensor and light incident on an insensitive portion between the elements is converged on the light receiving elements serving as a photosensitive portion on the surface of the sensor, i.e., a so-called micro-lens film is mounted on the surface of the sensor, is put to practical use. This micro-lens film is employed as the protection film of the photosensitive portion as it is, or a transparent solid layer lower in refractive index than this micro lens film is covered on the micro lens and the surface of the sensor is flattened, thereby facilitating the contact of a fingerprint with the surface of the sensor. The micro lens layer is advantageous if the light amount of a fingerprint measured portion is small or the power of a light source is to be reduced.

It is important that the lightness of the fingerprint ridgeline portion is as uniform as possible over the entire surface of the fingerprint measured portion so as to decrease a correction step in a later fingerprint image processing. Therefore, it is necessary to devise the arrangement of the light source so that the light injected into the finger is scattered in the finger and emitted from all the fingerprint ridgeline portions as uniform as possible. To do so, it is desirable to irradiate light to the finger from many directions. Namely, it is necessary to apply light to the finger from at least the front and rear of the fingerprint measured portion, i.e., the lower portion of the tip end of the fingertip and that of a portion close to the first joint of the finger.

To irradiate light to the finger from the most directions, a surface light emission body is arranged around the fingerprint measured portion so that the emitted light is directed toward the finger and a shield is provided around the measured portion so that the light emitted from the surface light emission body does not directly enter the measured portion. The reason for using the surface light emission body is to make the light source surround the measured portion. To fulfill the same purpose, a so-called linear light emission body formed by linearly arranging, for example, light emission diode chips may be used in place of the surface light emission body. Such a linear light emission body has sufficient light amount and serves as a thin, efficient light source. Since a module of such a linear light emission body has been recently supplied at low cost as a light emission diode chip array, the linear light emission body is highly practical.

The fingerprint verification based individual identification method has long been studied and it is the most practical among various individual identification methods. However, if a finger replica is formed out of a material similar to the finger cortex, the fingerprint of a subject person cannot be discriminated from that of the replica by optical images thereof taken by the two-dimensional image sensor. It is, therefore, necessary to acquire information as to whether or not a measurement target finger is a part of a human body before fingerprint verification. According to a fingerprint input method utilizing light transparency, attention is paid to the fact that the average lightness of the entire fingerprint image pulsates, and a function of determining whether or not the waveform of the pulsation is peculiar to a human body is additionally provided, whereby such determination information can be acquired.

The present invention has two basic structures, i.e., (1) a structure in which a transparent solid film having a thickness sufficiently less than the distance between fingerprint ridgelines is closely attached, as the transparent protection film of a two-dimensional image sensor, to the surface of the sensor, and (2) a structure in which a film obtained by perforating penetrating holes each having a diameter sufficiently smaller than the distance between the fingerprint ridgelines or penetrating holes aligned to the individual light receiving elements of the two-dimensional image sensor and by filling a transparent solid material into the holes, is fixedly attached to the surface of the sensor.

BRIEF DESCRIPTION OF THE DRAWINGS

FIG. 11 is a graph showing the relationship between the ratio of the thickness of the transparent solid film to the distance between fingerprint ridgelines and the contrast $C_1$ in a case where the contrast $C_0$ is 60%;

FIG. 13 is a conceptual view showing the basic configuration of a fingerprint input device according to the present invention;

DESCRIPTION OF THE PREFERRED EMBODIMENTS

Embodiment 1

Figure 1:
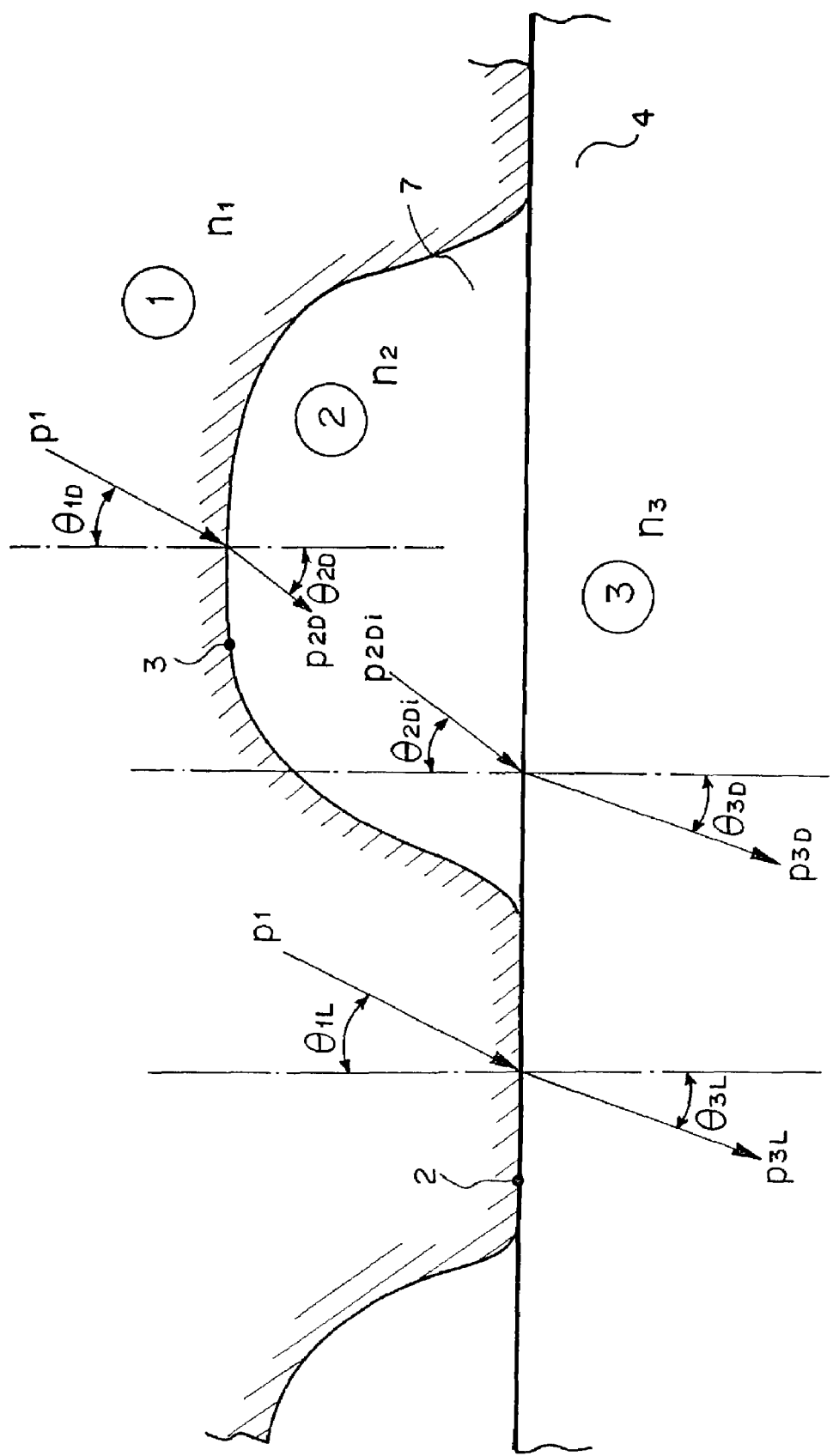
FIG. 1 is a fragmentary sectional view showing a model used to consider the relationship between the refractive index of a transparent solid film and contrast and showing a state in which a fingerprint measured portion is mounted on the transparent solid film.
Figure 2:
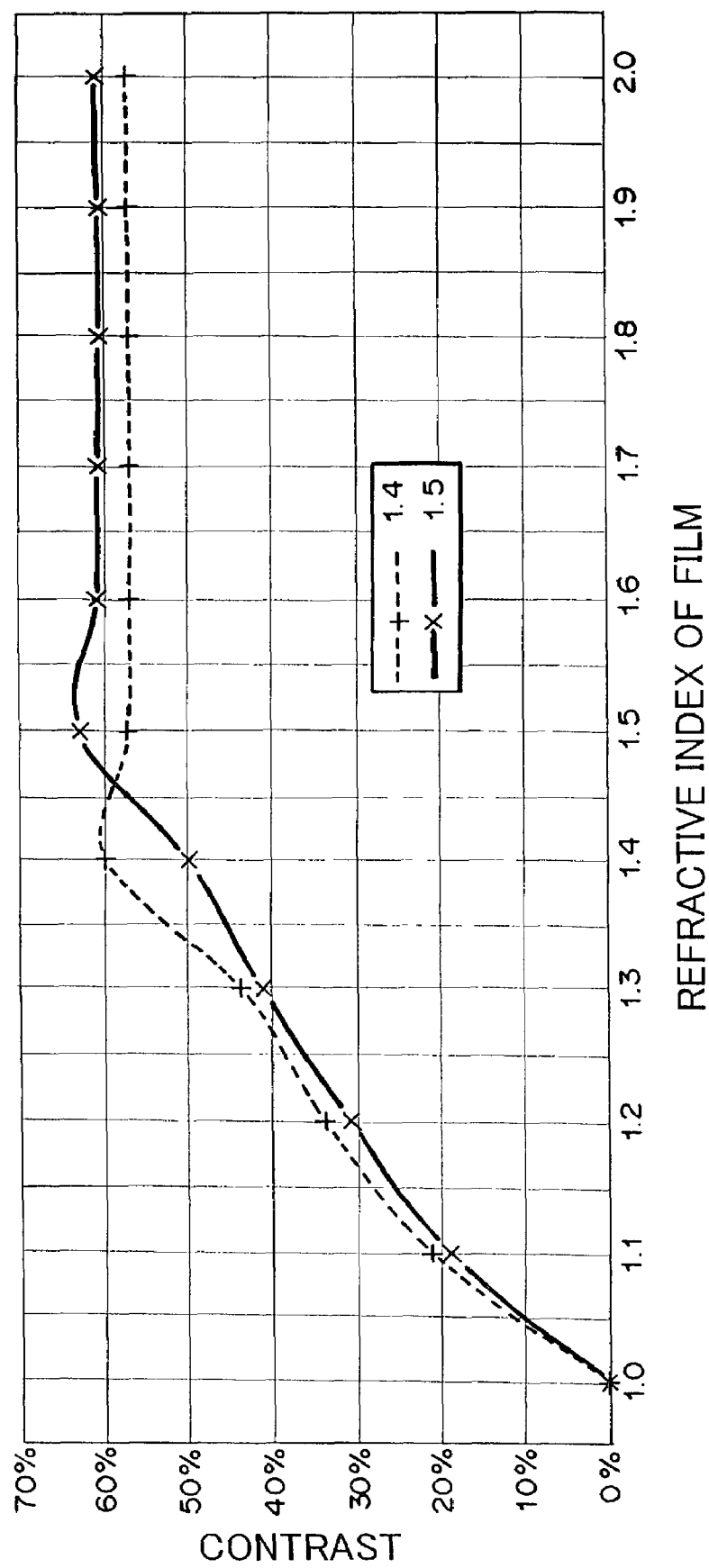
FIG. 2 is a first graph showing the relationship between the refractive index of the transparent solid film and the contrast.
Figure 3:
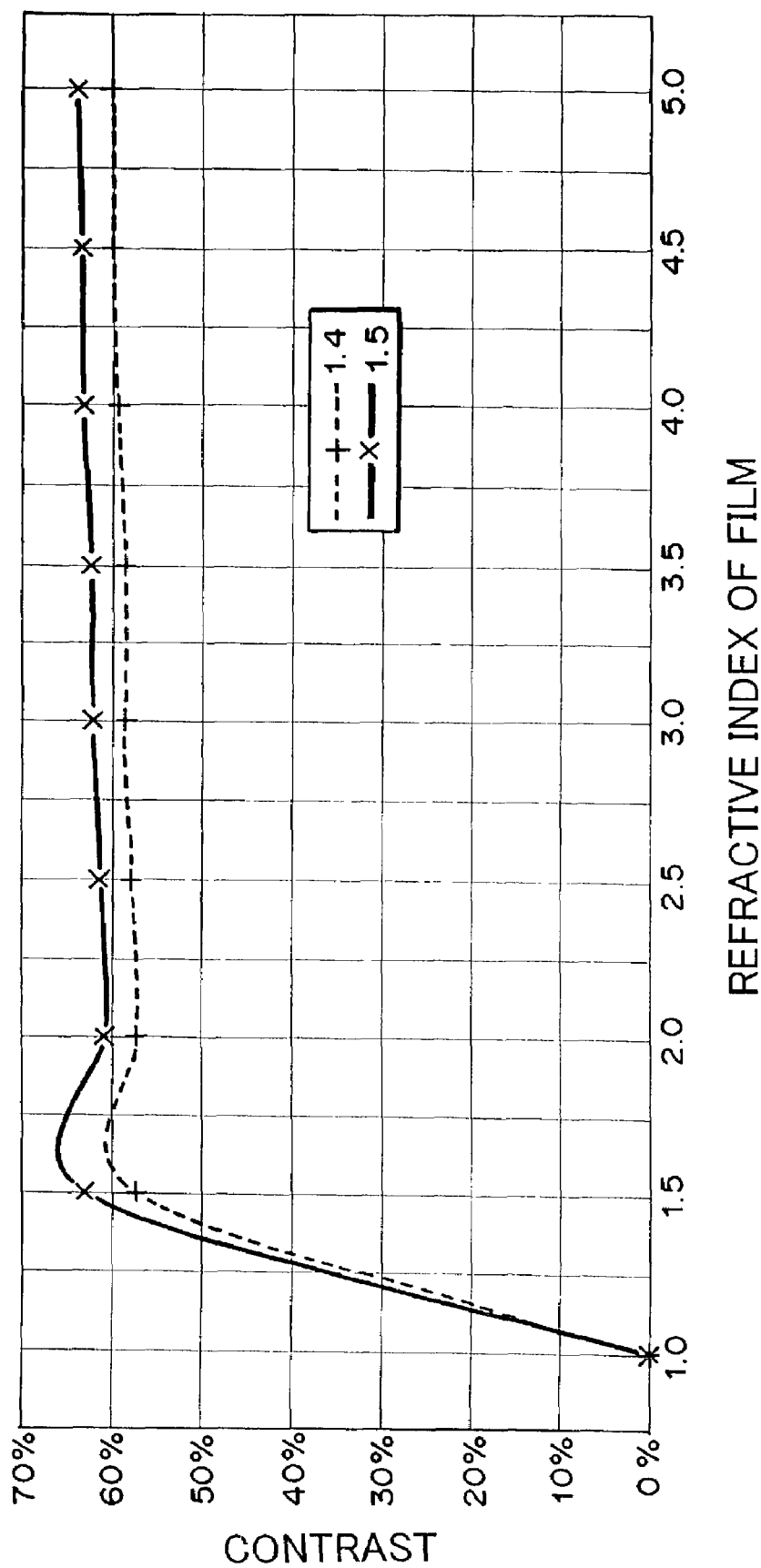
FIG. 3 is a second graph showing the relationship between the refractive index of the transparent solid film and the contrast.
Figure 4:
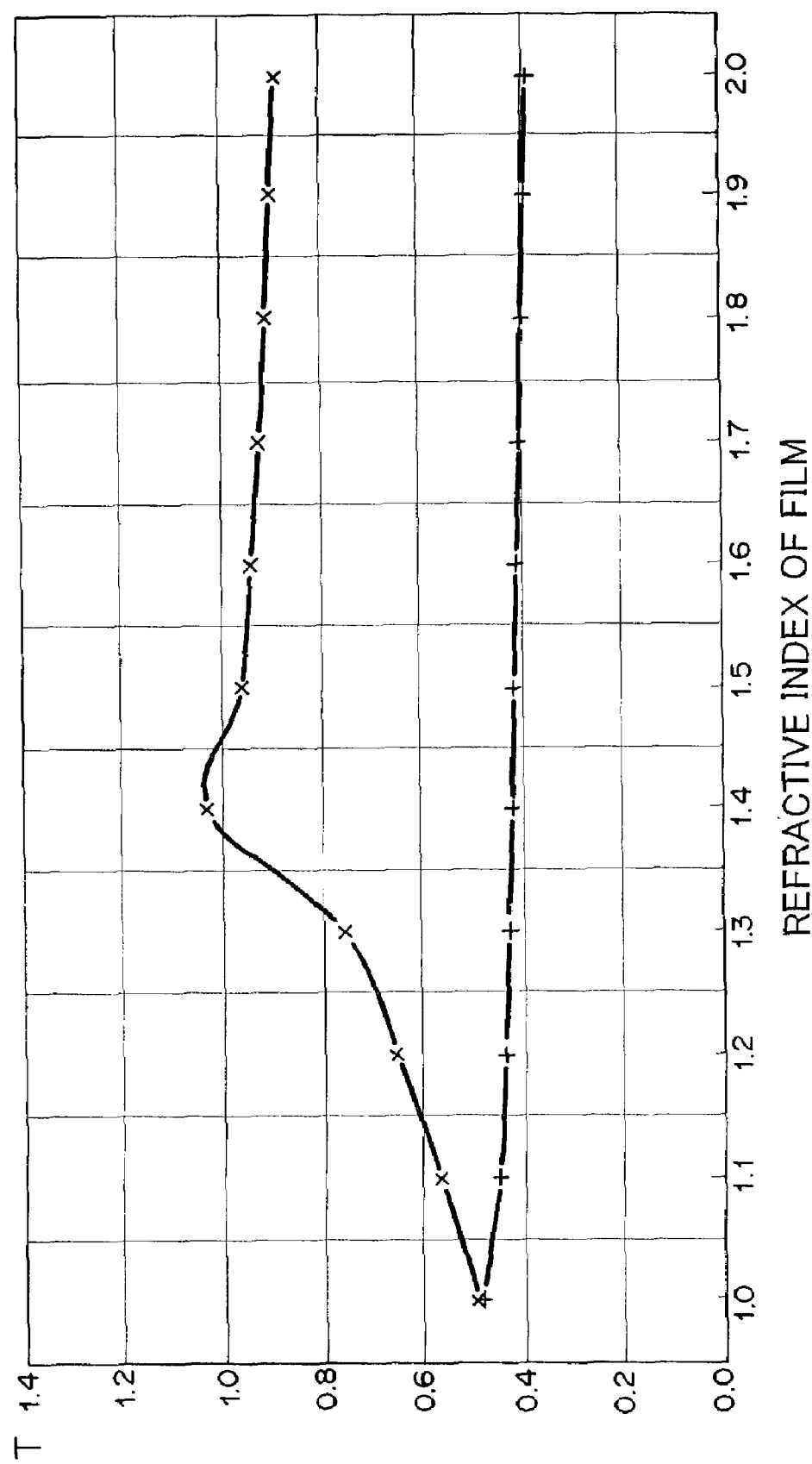
FIG. 4 is the first graph showing the relationship between the refractive index of the transparent solid film and transmittance in a case where the refractive index of a finger is 1.4.
Figure 5:
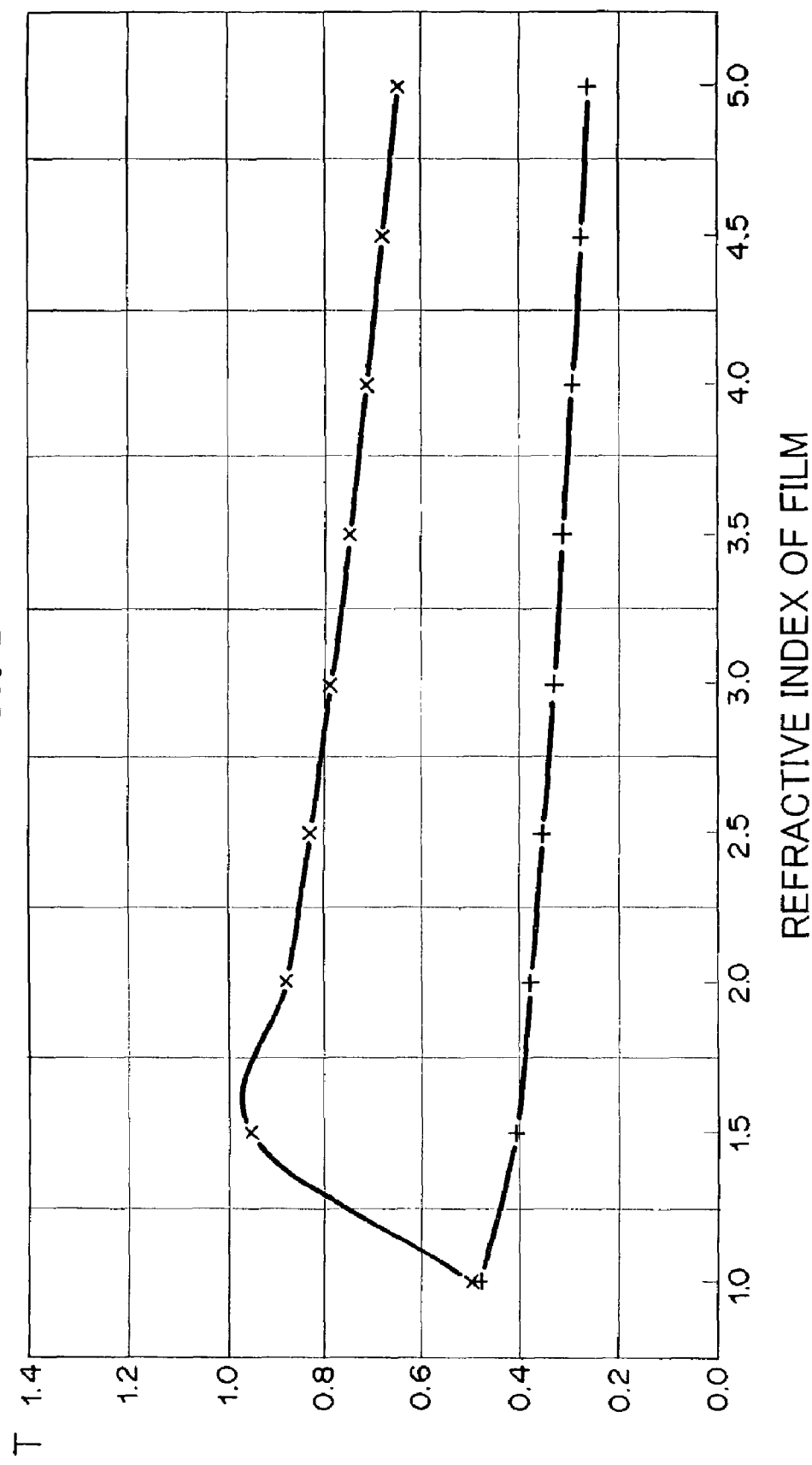
FIG. 5 is the second graph showing the relationship between the refractive index of the transparent solid film and transmittance in a case where the refractive index of a finger is 1.4.
Figure 6:
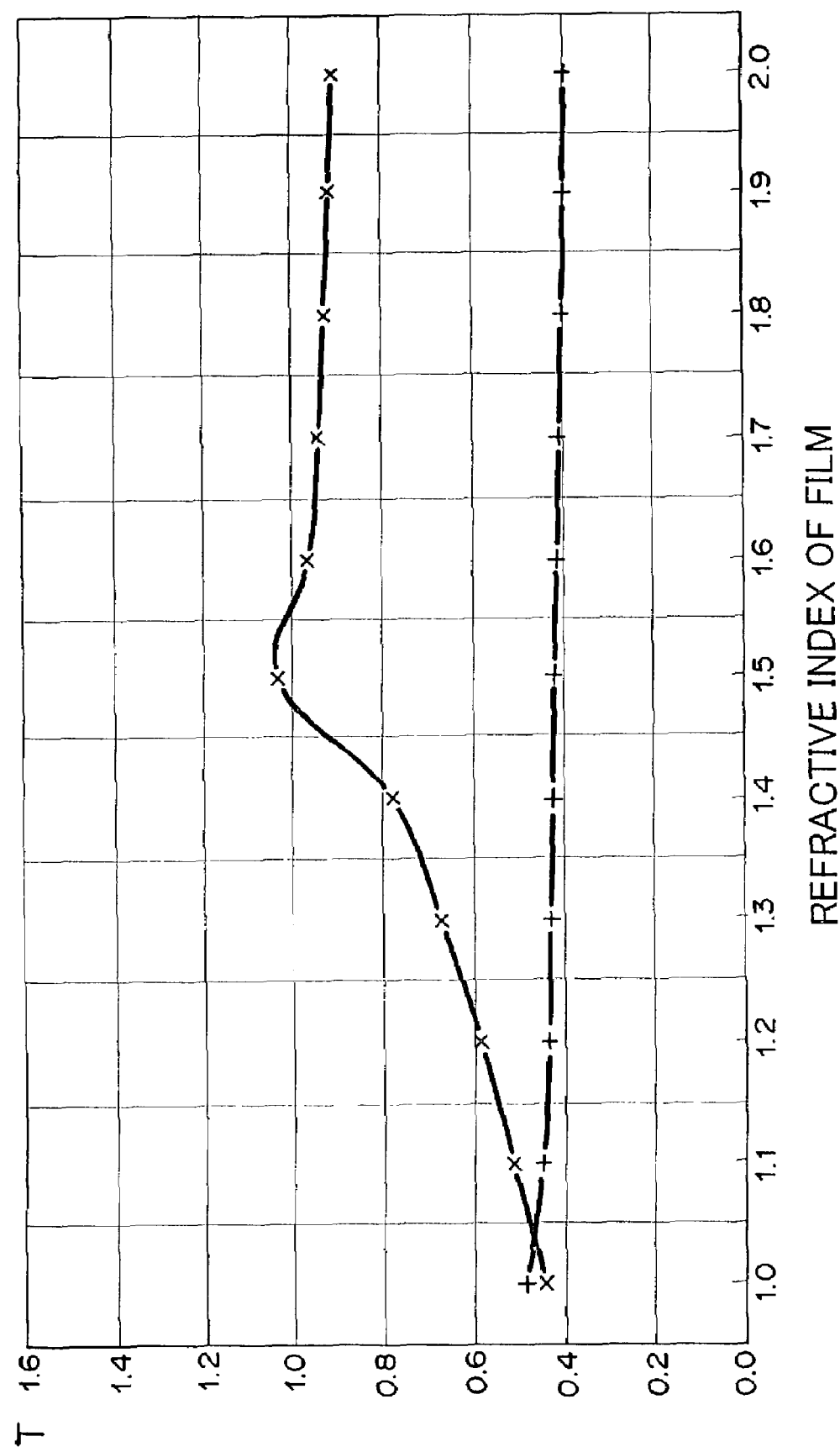
FIG. 6 is the first graph showing the relationship between the refractive index of the transparent solid film and transmittance in a case where the refractive index of a finger is 1.5.
Figure 7:
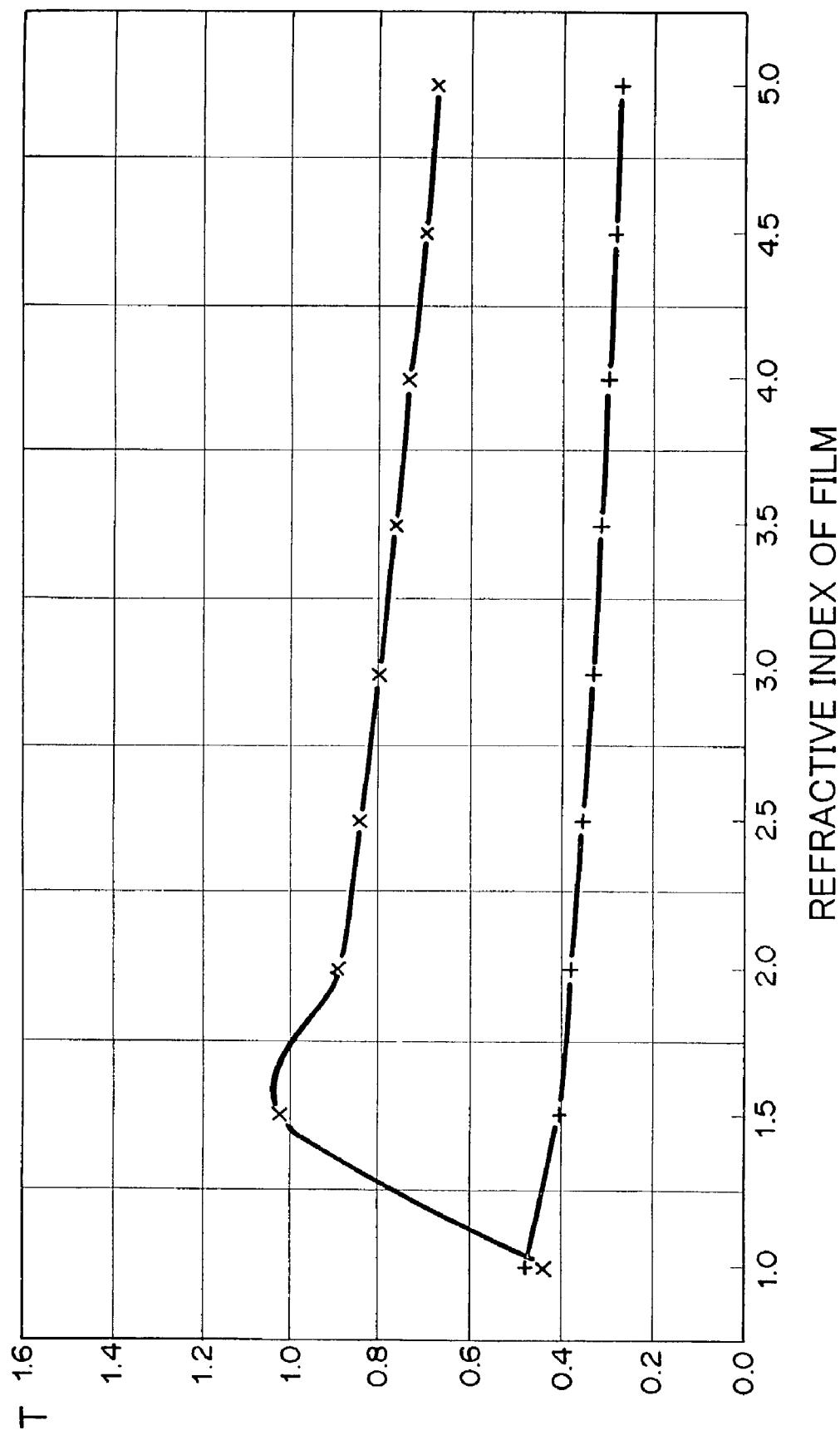
FIG. 7 is the second graph showing the relationship between the refractive index of the transparent solid film and transmittance in a case where the refractive index of a finger is 1.5.
Figure 8:
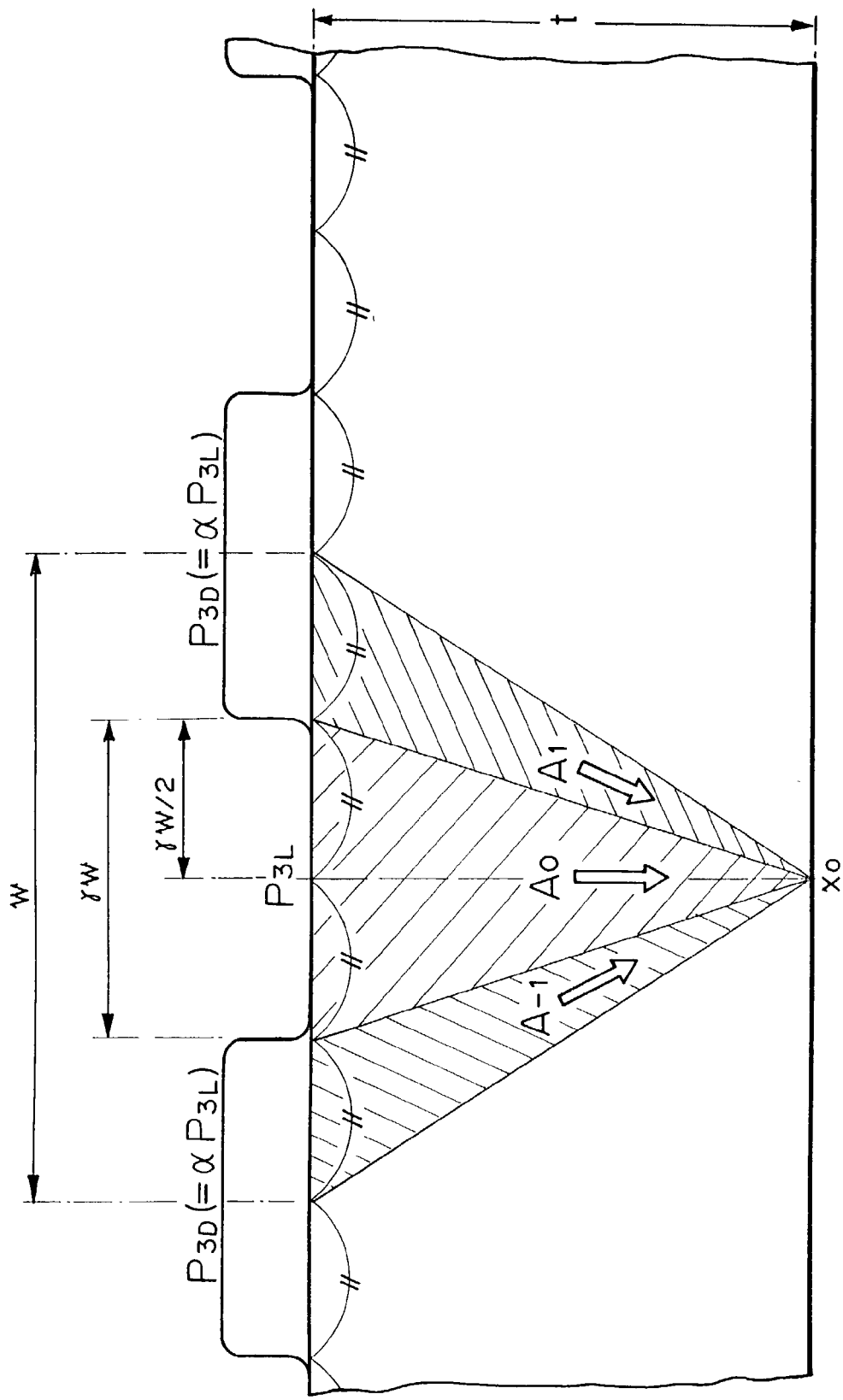
FIG. 8 is a typical view showing light received at a point $X_0$ right under the central point of a fingerprint ridgeline portion.
Figure 9:
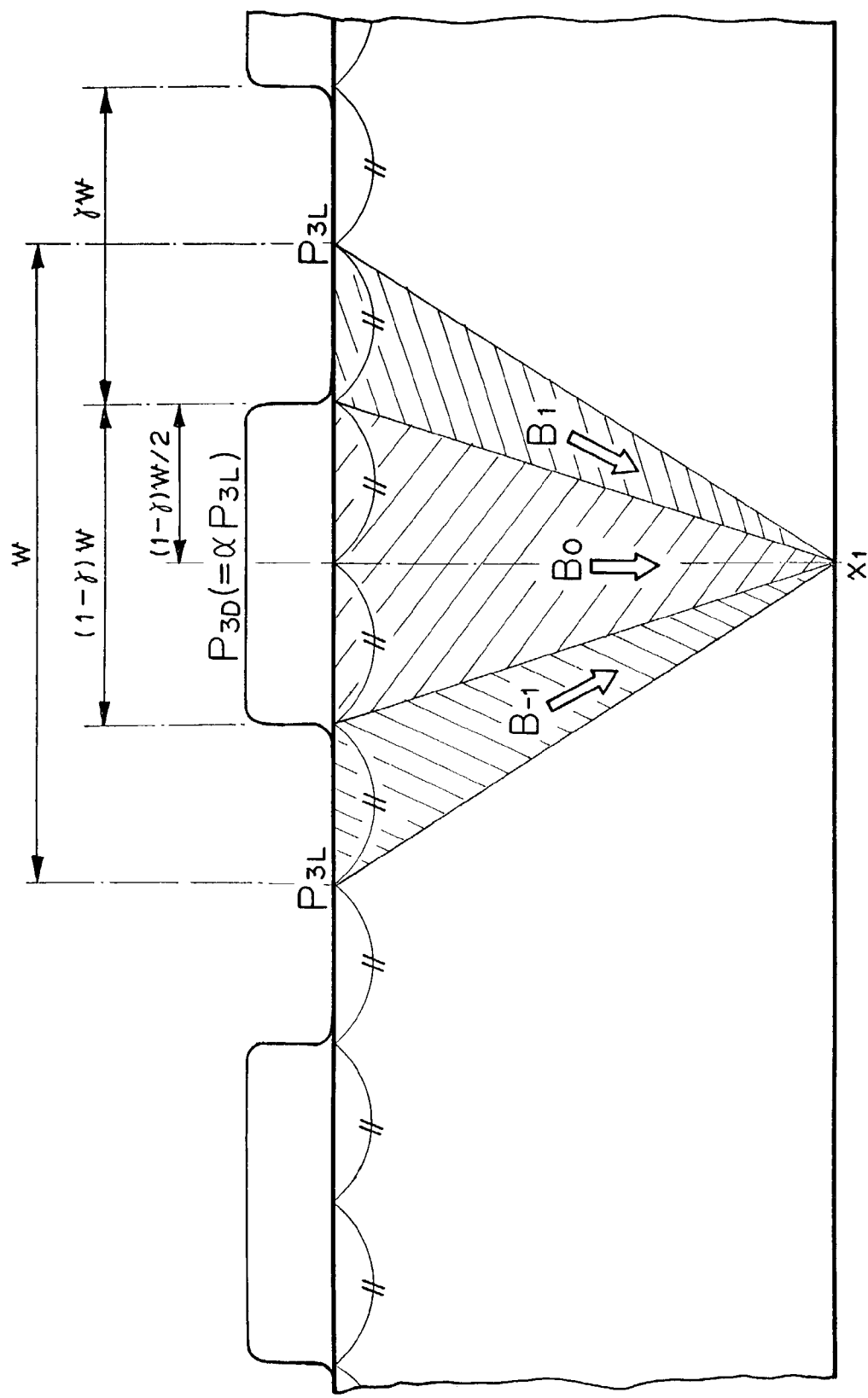
FIG. 9 is a typical view showing light received at a point $X_1$ right under the central point of a fingerprint valley portion.
Figure 10:
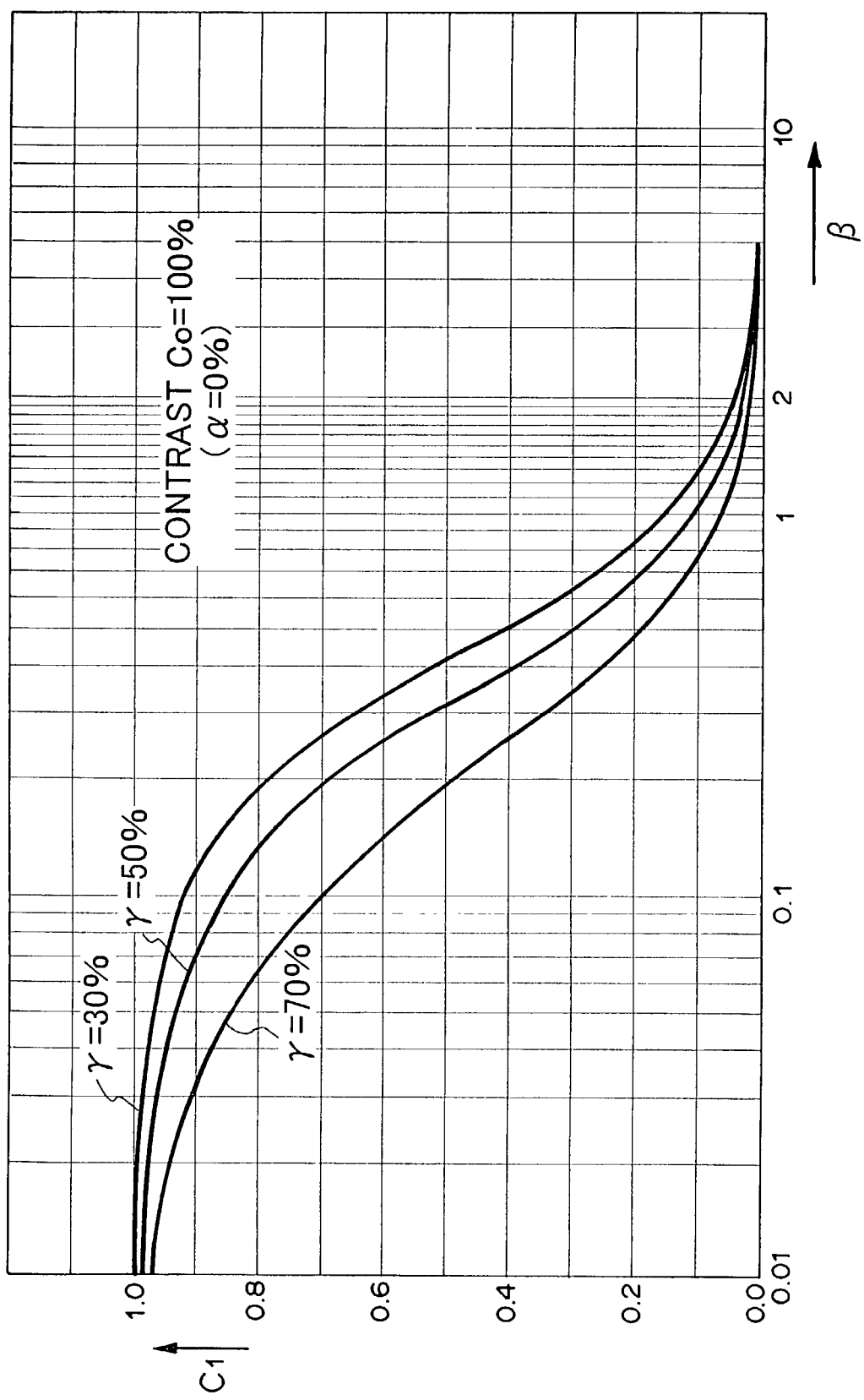
FIG. 10 is a graph showing the relationship between the ratio of the thickness of the transparent solid film to the distance between fingerprint ridgelines and contrast $C_1$ in a case where contrast $C_0$ is 100%.
Figure 12A:
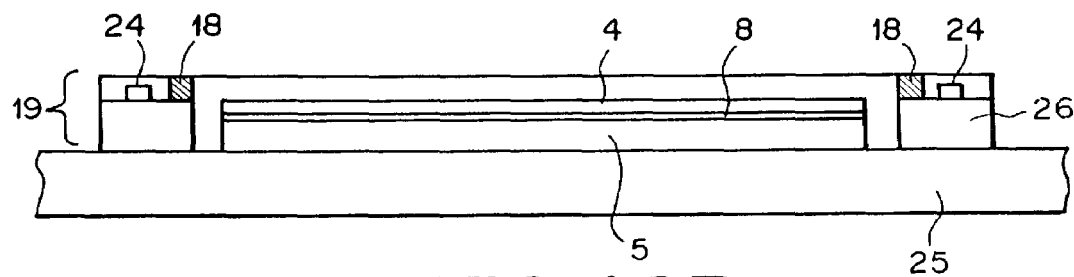
FIG. 12A shows a fragmentary sectional view of a prototype of a fingerprint input device according to one embodiment of the present invention.
Figure 12B:
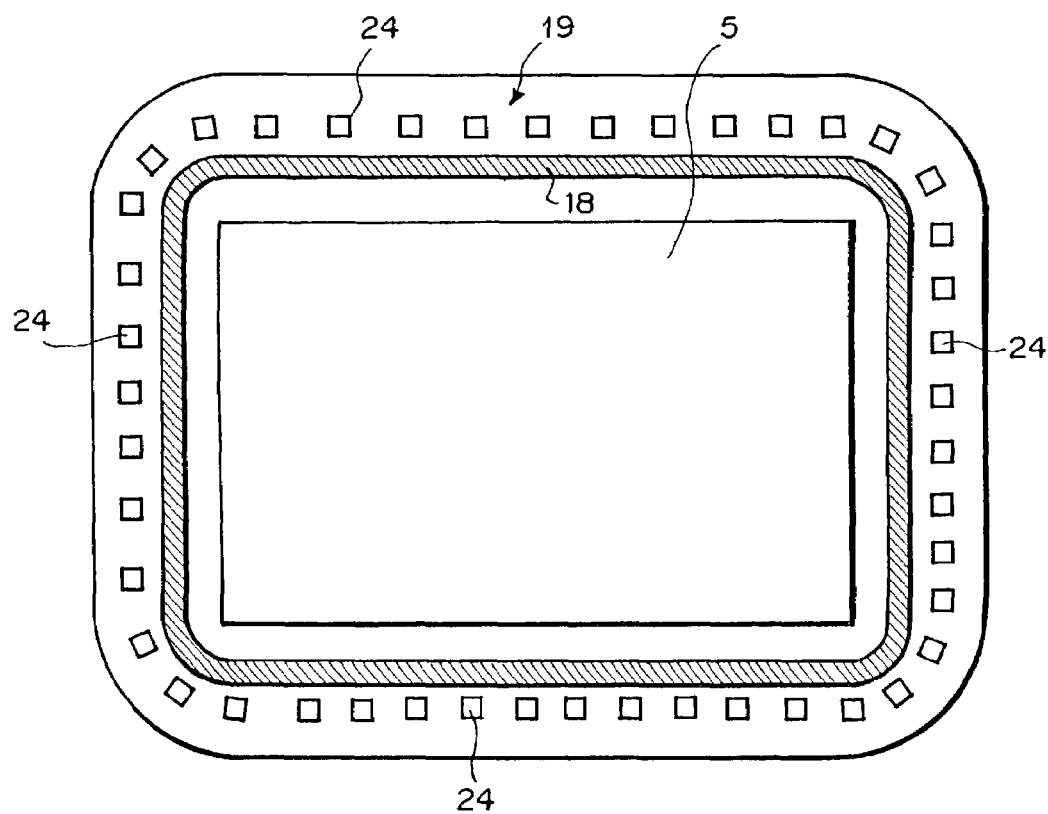
FIG. 12B shows a plan view of a prototype of a fingerprint input device according to one embodiment of the present invention.
Figure 14:
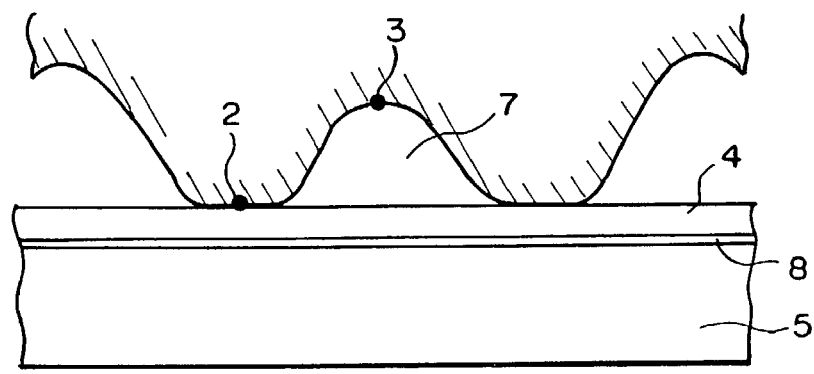
FIG. 14 is a fragmentary sectional view showing a state in which a fingerprint measured portion is mounted on a fingerprint input device according to Embodiment 1 of the present invention.
Figure 15:
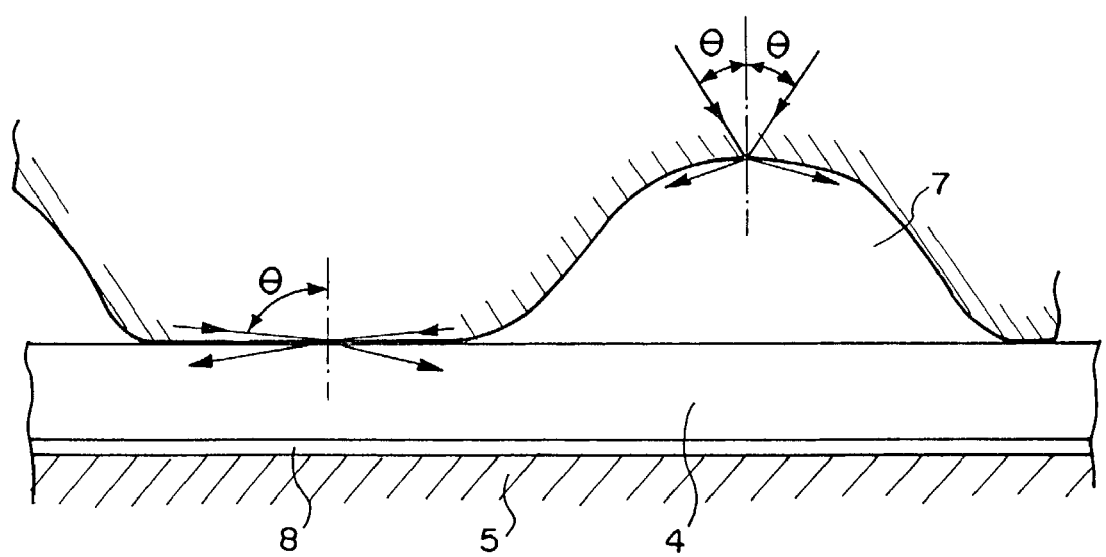
FIG. 15 is an enlarged fragmentary sectional view showing a state in which the fingerprint measured portion is mounted on the fingerprint input device according to the present invention.

FIGS. 12A and 12B show Embodiment 1 in which a very thin fingerprint input device according to the present invention is mounted on a printed circuit board. FIGS. 13, 14 and 15 show the operation states (operation principles) for fingerprint sensing when using the fingerprint input device, respectively.

FIG. 13 is a block diagram showing the configuration of the fingerprint input device according to Embodiment 1 of the present invention. In FIG. 13, reference numeral 5 denotes a two-dimensional image sensor which two-dimensionally detects the strength and weakness of light depending on the irregularities of a finger 1, 27 denotes an image processing portion which generates a fingerprint pattern by subjecting the output of the two-dimensional sensor 5 to an image processing, and 28 denotes a pattern recognition portion which extracts the feature of the fingerprint pattern generated by the image processing portion 27, compares the extracted feature with a predetermined reference pattern and thereby recognizes and determines the fingerprint pattern.

A case where a CMOS (Complementary Metal Oxide Semiconductor) sensor, a CCD (Charge-Coupled Device) sensor or an amorphous sensor is used as the two-dimensional image sensor 5 will be described hereinafter by way of example. It is noted that a normally used image processing portion and a normally used pattern recognition portion can be applied as the image processing portion 27 and the pattern recognition portion 28, respectively.

The two-dimensional image sensor 5 is constituted of many light receiving elements arranged two-dimensionally. A plane image is formed based on the outputs of these light receiving elements. It is necessary that the arranged distance between the light receiving elements is less than the pitch of fingerprint ridgeline portions (convex portions) or that of fingerprint valley portions (concave portions). However, since the distance between the fingerprint ridgeline portions is 100 to 500 μm, an image having sufficient accuracy for pattern recognition can be obtained if the arranged distance between the light receiving elements is set at 50 μm or less.

FIG. 14 is an explanatory view showing the light receiving process of the two-dimensional image sensor. When the fingerprint of a finger 1 is to be input, the finger 1 is put on the two-dimensional image sensor 5 so that the fingerprint ridgeline portions contact a transparent solid film 4 on the two-dimensional image sensor 5. This transparent solid film 4 is formed out of a transparent member, e.g., glass, having the above-stated refractive index according to the present invention. In addition, the transparent solid film 4 has a function of preventing a fingerprint measured portion from directly contacting the two-dimensional image sensor. This function can prevent the two-dimensional image sensor from being worn and broken even if the fingerprint input device is used a number of times. Further, the transparent solid film 4 has wear resistance to the extent that the film 4 is not worn due to friction with the finger.

The fingerprint ridgeline portion 2 contacts the transparent solid film 4 on the two-dimensional image sensor 5. In addition, since the refractive index of the finger 1 is almost equal to that of the transparent solid film 4, almost all scattered light directed from the fingerprint ridgeline portion 2 toward the transparent solid film 4 is incident on the transparent solid film in the fingerprint ridgeline portion 2.

Meanwhile, a space 7 is present between the fingerprint valley portion 3 and the transparent solid film 4. Since the difference between the refractive index of the finger cortex (about 1.4 to 1.5) and that of the air (1.000293) is large, most of the scattered light from the fingerprint valley portion 3 to the space 7 is reflected by the skin and irradiated to the finger and the scattered light from the fingerprint valley portion 3 to the space 7 at an angle equal to or larger than a critical angle is all reflected and enters the finger. Accordingly, the amount of the light incident on the space 7 from the fingerprint valley portion 3 is very small. Further, because of the large difference between the refractive index of the air (1.000293) and that of the transparent protection film, most of the light directed from the space 7 toward the transparent protection film 4 is reflected. Therefore, the amount of the light incident from the fingerprint valley portion to the transparent protection film 4 is less than that of the light incident from the fingerprint valley portion to the space 7.

Accordingly, the two-dimensional image sensor satisfactorily detects light from the fingerprint ridgeline portion 2 and hardly detects light from the fingerprint valley portion 3, so that the sensor detects the fingerprint ridgeline portion 2 as a light portion and the fingerprint valley portion 3 as a dark portion.

According to the present invention, therefore, it is unnecessary to provide optical components such as a lens, a prism and an optical fiber. Compared with the conventional fingerprint input device, no restriction is imposed on the physical magnitude of the device due to the magnitude of the optical component themselves and attachment locations of the components. It is, therefore, possible to realize a thin, small fingerprint input device so as to be capable of being mounted on the interior of an IC card or the like which requires the authentication of the user of the card. If the fingerprint input device is mounted on an article which is thin and highly easy to bent such as an IC card, and a two-dimensional image sensor 5 formed out of an amorphous semiconductor grown on a flexible substrate film by evaporation or the like is employed as the two-dimensional image sensor 5, then the image sensor can resist a large degree of bending. In this case, a flexible film is used as the transparent solid film 4, as well. The flexible transparent solid film is exemplified by a polyimide film or a polycarbonate film. Considering that the refractive index of polyimide is about 1.4 and that of polycarbonate is about 1.55, and that polycarbonate is strong enough to resist the use thereof, it is preferable to use the polycarbonate film as the flexible transparent solid film.

Furthermore, according to the present invention, an optical processing is not carried out using the optical components. Therefore, it is possible to obtain a distortion-free fingerprint image without need to execute an image correction processing such as distortion correction, and to improve a fingerprint pattern recognition rate.

Since the transparent solid film needs to have sufficient wear resistance so as not to be worn even if the finger repeatedly contacts the film, a vitreous matter or an organic matter having a refractive index according to the present invention and hard to be scratched is used as the material of the transparent solid film. However, most of vitreous matters and organic matters are not conductive. Since the fingerprint input device of the present invention is an optical fingerprint input device, there is less possibility of electrostatic breakdown due to the static electricity of the finger. However, it is preferable to relieve the static electricity to protect the two-dimensional image sensor which is a semiconductor element from the electrostatic breakdown. To do so, it is preferable that a transparent, conductive thin film made of tin oxide, ITO or the like is formed on the transparent solid film and the conductive thin film is grounded as stated above.

Figure 16:
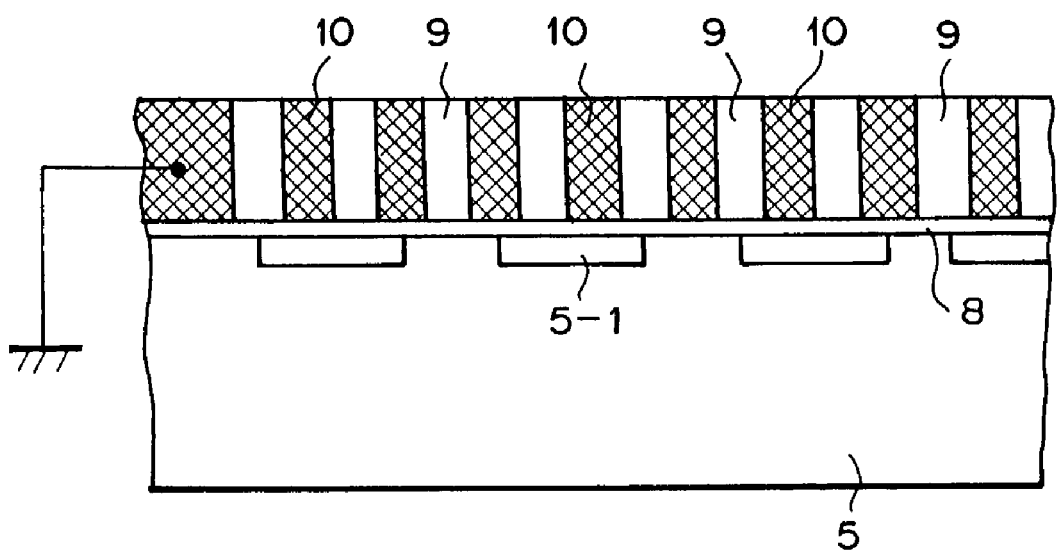
FIG. 16 is a fragmentary sectional view showing the structure of a fingerprint input device according to Embodiment 2-1 of the present invention.
Figure 17:
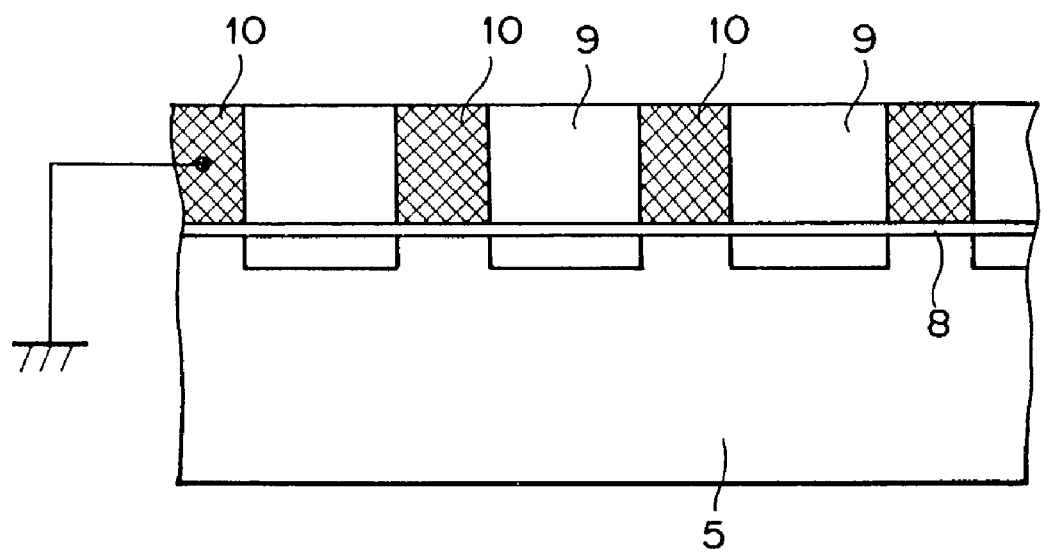
FIG. 17 is a fragmentary sectional view showing the structure of a fingerprint input device according to Embodiment 2-2 of the present invention.

If a light shielding wall shown in FIGS. 16 and 17 to be described later is employed, it is possible to relieve strong static electricity by using metal as the material of the light shielding wall and grounding the wall. The fingerprint input devices shown in FIGS. 16 and 17 are excellent in light of the prevention of the device from static electricity if being used outdoors.

In addition, since the fingerprint input device of the present invention is a light transmission type device, disturbance light also functions as the light source of transmission light and less adversely influences the fingerprint input device. However, to ensure stable fingerprint detection even if disturbance light is extremely strong or disturbance light enters from the gap between the fingerprint measured portion and the surface of the fingerprint input device, it is effective that the light source emitting light in a specific waveband is designed to irradiate light to portions of the fingertip other than the fingerprint measured portion, and that a spectroscopic filter which passes through only the light in the waveband is provided at a certain position between the two-dimensional image sensor and the surface of the fingerprint input device whereby the waveband of the light used for fingerprint measurement is narrowed and the disturbance light is cut off. By way of example, a near-infrared ray emission diode is used as a light source and a near-infrared filter having the same transmission wavelength as the emission wavelength of the diode is used as a spectroscopic filter. In this case, the near-infrared ray tends to be transmitted into a living body, particularly, the skin. If a wavelength of 800 to 950 nm is selected, the absorption coefficient of blood for the near-infrared ray in this wavelength is about 10%. Therefore, a living body can be sensed by the pulsation of the transmission light without deteriorating measurement sensitivity. The infrared ray or the like having a wavelength 1400 nm or more includes a waveband in which the infrared ray or the like is absorbed by water depending on the wavelength. It is necessary to avoid using the infrared ray having waveband in that range. Further, in a waveband in which the light absorption coefficient of the blood for light including disturbance light is too low, the filter becomes sometimes insensitive to the pulsation of the blood for the sensing of a living body. For this reason, it is also necessary to avoid this waveband. These notes are common to the selection of the light emission diode serving as the light source and the spectroscopic filter which passes through only the light from the diode.

Embodiment 2

Embodiment 2 will next be described. FIGS. 16 and 17 are fragmentary sectional views of two kinds of fingerprint input devices according to Embodiment 2. A cover film 8 of a two-dimensional image sensor is intended to stabilize the characteristic of the sensor element, should be formed in a semiconductor manufacturing process and is normally thinner than several micrometers due to a semiconductor device manufacturing method used. If the finger is repeatedly, directly pressed against the cover film 8, the durability of the film 8 is adversely influenced by the contact of the finger. Therefore, in Embodiment 1, a transparent solid film 4 is provided and the thickness, refractive index and hardness of the transparent solid film 4 are specified. Among them, it is the thickness condition that contradicts the durability condition. Namely, as the transparent solid film 4 is thinner, a clearer image is obtained. As the transparent solid film 4 is thicker, the durability of the film improves. To obtain the contrast of a fingerprint image, if the minimum distance between fingerprint ridgeline portions is 100 μm, the thickness of the transparent solid film 4 can be increased up to, for example, 60 μm. If the thickness of the transparent solid film 4 is 60 μm, the durability thereof is sufficient as long as the device is normally used. However, if the device is used while being exposed to the weather outdoors, the transparent solid film 4 is preferably thicker further. Nevertheless, if the transparent solid film 4 becomes too thick, the fingerprint input device in Embodiment 1 cannot obtain the contrast of the fingerprint image.

The problem of Embodiment 1 is solved by the structure of Embodiment 2 shown in FIGS. 16 and 17. If the transparent protection film 8 is too thick, the components of light directed to a horizontal direction increase and the clearness of fingerprint ridgelines deteriorates. To prevent the deterioration, a light shielding wall is provided in a vertical direction to shield the light in the horizontal direction. FIG. 16 shows an example in which the light shielding walls are close in order to make it unnecessary to align the hole to the respective elements of the two-dimensional image sensor. FIG. 17 shows an example in which the light shielding walls are aligned with the pitch of the elements of the two-dimensional image sensor, thereby making it unnecessary to make the walls close.

In the fingerprint detection device shown in FIG. 16, many penetrating holes, diameters of which are not longer than a half of the light receiving diameter of each light receiving element of the two-dimensional image sensor, are formed in a film of a light shielding material such as metal and the composition of the transparent solid film (to be referred to as "transparent solid material" hereinafter) is filled into the penetrating holes so that at least one penetrating hole corresponds to each light receiving element to shield the element without the need to align the penetrating holes surrounded by the light shielding wall to the light receiving elements of the two-dimensional image sensor, respectively, whereby the transparent solid film having the light shielding wall is formed. The transparent solid film having the light shielding wall is then closely attached to the surface of the two-dimensional image sensor. In this case, there is no need to align the penetrating holes to the respective light receiving elements of the two-image sensor, facilitating assembly. However, if the pitch of the light receiving elements of the two-dimensional image sensor is 50 μm and the light receiving diameter of each element is 25 μm, then it is necessary to set the diameter of each penetrating hole at 12.5 μm or less. If the thickness of the light shielding wall is considered, the walls are preferably closer.

If the outdoor use of the device is considered, it is preferable that the thickness of the transparent solid film having the light shielding wall is 60 μm or more. As a result, the penetrating holes become deep like wells. To fill the penetrating holes with the transparent solid material, a relatively advanced film formation method is required.

According to the fingerprint detection device shown in FIG. 17, by contrast, a film of a light shielding material having penetrating holes in which the magnitude, shape and position of each of which is completely consistent with those of the light receiving surface of each light receiving element of the two-dimensional image sensor is formed, a transparent solid material is filled into the penetrating holes of this light shielding film, and the light receiving surfaces of the light receiving elements of the two-dimensional image sensor are aligned with the penetrating holes, respectively, thereby assembling the detection device. According to the method for manufacturing this fingerprint detection device, it is required to ensure particularly high accuracy to satisfy the positional relationship between the light receiving surfaces of the light receiving elements and the penetrating holes. However, if the pitch of the light receiving elements of the image sensor is 50 μm and the light receiving diameter of each element is 25 μm, then it suffices that the diameter of each penetrating hole is 25 μm. Therefore, even the shielding film having a thickness of 60 μm can be easily manufactured.

As long as the light absorption coefficient of the transparent solid material filled into the penetrating holes is low, the clearness of a fingerprint image basically has no change even if the clearness of the transparent solid material is low, i.e., even if light is scattered in the penetrating holes. This fingerprint detection device basically differs in this respect from the device using an optical fiber flux.

That is, the optical fiber has a core and a clad so as to suppress the deterioration of signal transmission performance due to the zigzag movement of light. If light is incident on the optical fiber from the end face of the optical fiber, a critical incidence angle exists and the optical fiber only guides the light having a limited incidence angle and transmits the light in this angle range without dispersing the light in the horizontal direction. In other words, the light incident on the optical fiber has good rectilinear propagation property when the light is emitted from the optical fiber.

Therefore, the light incident on the optical fiber is emitted at the same angle as the incidence angle. However, light is not incident on the optical fiber from microscopic concave portions on the end of the fingerprint ridgeline portion and no compensation is made by horizontal light, with the result that a ridgeline image tends to be intermittent.

On the other hand, if the transparent solid film of the present invention is used, no critical angle exists for the incidence angles of the light from the fingerprint ridgeline portion to the transparent solid film irrespectively of whether or not the transparent solid film has a light shielding wall. As a result, if the horizontal components of the light from the microscopic irregular portions on the end of the fingerprint ridgeline portions are incident into the transparent solid film and, therefore, light is propagated to the photosensitive portion of the two-dimensional image sensor from the transparent solid film, then the image missing parts corresponding to the microscopic irregular portions are compensated by the light of horizontal components. Therefore, the apparent clearness of a fingerprint image is deteriorated.

Further, if a sweat gland is present in a fingerprint ridgeline portion, it appears on an image as a dark region due to the presence of the critical angle of the fingerprint ridgeline portion according to the fingerprint input device using the optical fiber. On the other hand, according to the fingerprint input device of the present invention, since no critical angle exists in the fingerprint ridgeline portion, no sweat gland appears on an image as a dark region. In view of this, the fingerprint input device using the transparent solid film of the present invention is advantageous over that using the optical fiber in a case where the fingerprint ridgeline portion is to be discriminated from the fingerprint valley portion. In other words, in a case where the fingerprint input device using the optical fiber is employed so as to discriminate the fingerprint ridgeline portion from the fingerprint valley portion, an image processing is required to eliminate the dark region of the sweat gland. If the fingerprint input device using the transparent solid film of the present invention is employed for the same purpose, no image processing is required to eliminate the dark region of the sweat gland.

Moreover, it is important to be capable of reading a ridgeline which is not intermittent so as to track the fingerprint ridgeline as the main process of a fingerprint verification operation. If the ridgeline becomes intermittent, an image processing block performs an intermittent ridgeline connection processing. However, this processing requires considerably large amount of calculation. It is, therefore, important to decrease the number of intermittent points as much as possible and to decrease the calculation amount as much as possible. For the same reason as above, the number of points at which the ridgeline is broken off increases according to the fingerprint input device using the optical fiber. On the other hand, according to the fingerprint input device using the transparent solid film of the present invention, there is no possibility that a ridgeline is unnecessarily broken off. The fingerprint input device of the present invention is, therefore, suited for fingerprint verification.

Each of the fingerprint input devices shown in FIGS. 16 and 17 suppresses the light in the thick film from advancing in the horizontal direction. However, the suppression of light is limited to the order of the distance between the fingerprint ridgelines. Therefore, the light incident on the thick film does contain horizontal components. This is different from a fingerprint input device using the optical fiber which is intended to suppress the horizontal components of the light.

Figure 18:
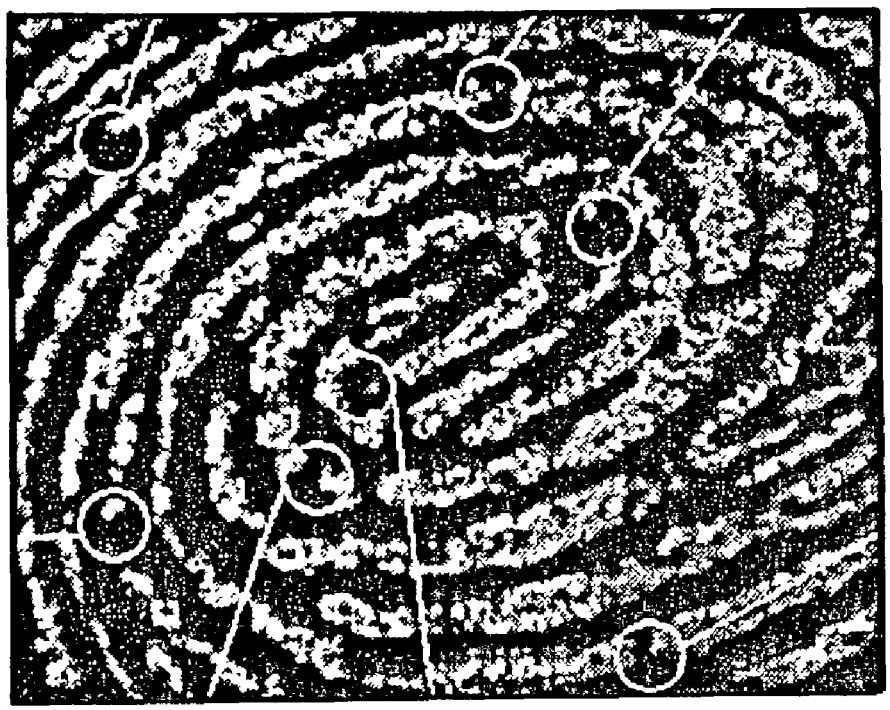
FIG. 18 shows a photograph of a fingerprint image taken by a light transmission type fingerprint input device employing an optical fiber (aperture rate of 0.35)
Figure 19:
FIG. 19 shows a photograph of a fingerprint image taken by a fingerprint input device according to the embodiment of the present invention.

The difference in the intermittence of the fingerprint ridgeline between the fingerprint input device using an optical fiber having an aperture rate of 0.35 and that of the present invention becomes clear by comparing a fingerprint image input by the former device shown in FIG. 18 with a fingerprint image input by the latter device shown in FIG. 19. Since the fingerprint image shown in FIG. 18 is clearer than that shown in FIG. 19, the former device appears superior to the latter device. However, it is seen that the latter device is superior to the former device in that missing points indicated by white circles shown in FIG. 18 do not appear in FIG. 19.

Embodiment 3

In Embodiment 3, a micro-lens layer which has been recently used to enhance the sensitivity of an image sensor is employed as a protection film.

Figure 20:
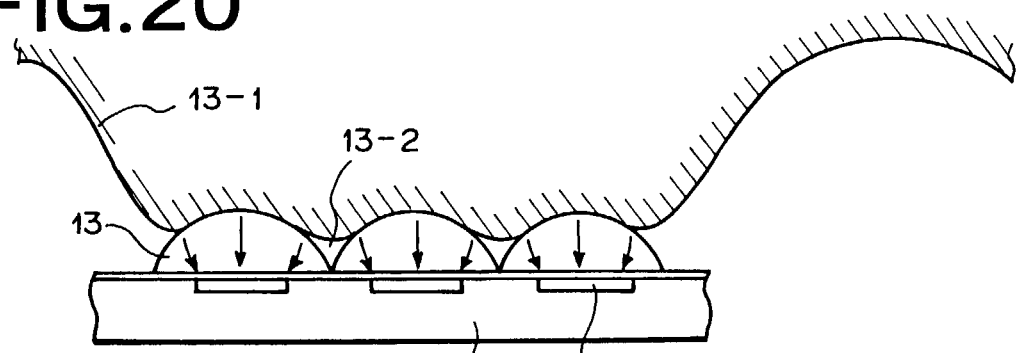
FIG. 20 is a fragmentary sectional view showing the structure of a fingerprint input device according to Embodiment 3-1 of the present invention.

In Embodiment 3, a micro-lens 13 as a dome-shaped transparent solid is covered right over the photosensitive portion of an image sensor as shown in FIG. 20, whereby light incident on portions other than the photosensitive portion is converged on the photosensitive portion and the light detection sensitivity of the sensor is enhanced. When a fingerprint ridgeline portion contacts the micro-lens 13, the ridgeline is shaped as indicated by 13-1 and the light detection sensitivity of the sensor is enhanced by the convergence of the light on the photosensitive portion. However, the light incident on the micro-lens 13 from a valley portion 13-2 is emitted once to a space and the light from this portion becomes unavailable. As a result, the light in the 100% region of the fingerprint ridgeline portion cannot be detected. Nevertheless, since a normally mass-produced sensor can be used as it is for the image sensor, the fingerprint input device in this embodiment is advantageous in cost. As the composition of the micro-lens 13, that of the transparent solid film in Embodiment 1 is used. Accordingly, the refractive index of the micro-lens is specified according to the present invention as in the case of the refractive index of the transparent solid film.

Figure 21:
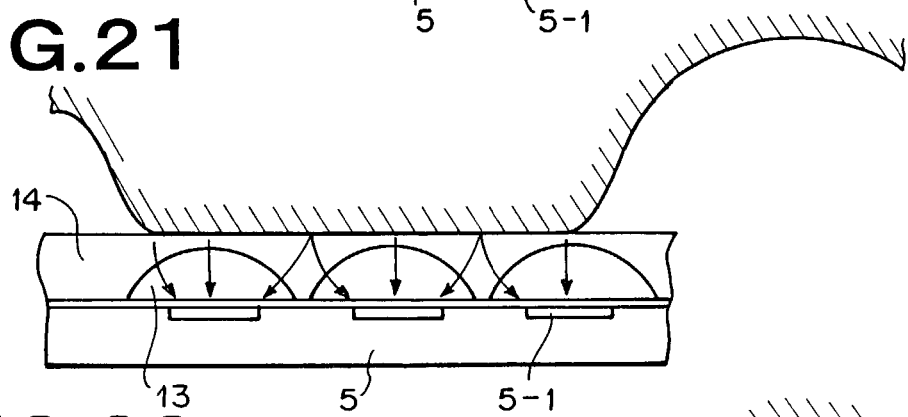
FIG. 21 is a fragmentary sectional view showing the structure of a fingerprint input device according to Embodiment 3-2 of the present invention.

A fingerprint input device shown in FIG. 21 is an improvement of the fingerprint input device shown in FIG. 20. The fingerprint input device shown in FIG. 21 employs a lamination lens so as to flatten a portion which the finger contacts. The lamination lens is obtained by laminating a transparent solid material 14 lower in refractive index than the material of the micro-lens on the micro-lens 13. It is noted that the transparent solid material 14 is the composition of the transparent solid film in Embodiment 1. Accordingly, the refractive index of the transparent solid material 14 is specified according to the present invention and the refractive index of the micro-lens 13 is higher than that of the transparent solid material 14.

According to the fingerprint input device shown in FIG. 21, it is possible to detect light from the 100% region of the fingerprint ridgeline portion because of absence of the valley portion 13-2. As a result, the light detection sensitivity of the sensor is enhanced. In addition, because there exists no thin valley portion in the micro-lens 13, the durability of the micro-lens 13 improves.

Figure 22:
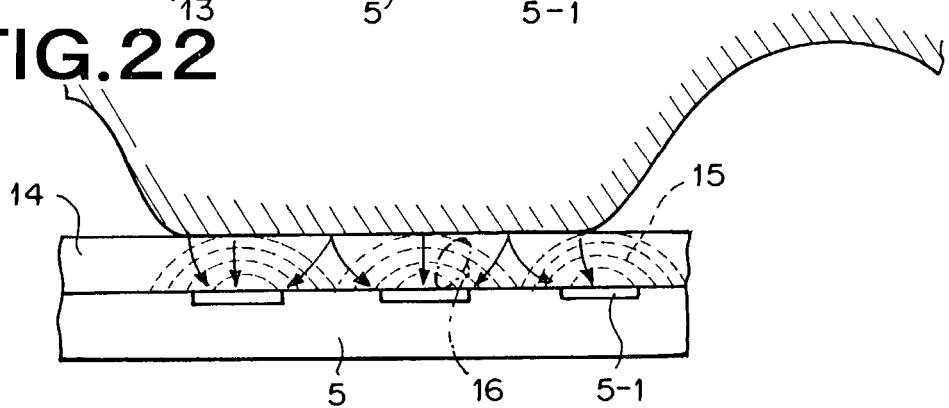
FIG. 22 is a fragmentary sectional view showing the structure of a fingerprint input device according to Embodiment 3-3 of the present invention.

A fingerprint input device shown in FIG. 22 employs, as a micro-lens, a flat micro-lens 15, the refractive index distribution of which is formed to be adjusted to the pitch of an image sensor. The flat micro-lens 15 is formed on a transparent solid film. The flat micro-lens 15 can be formed by injecting impurities into the points of the transparent solid film which contact the respective light receiving elements of a two-dimensional image sensor and diffusing the impurities when the transparent solid film is formed. The flat micro-lens 15, therefore, has a transmittance distribution 16 in which the transmittance is lower as the film is farther from the light receiving element. The flat micro-lens 15 is higher in light-gathering power than the micro-lenses 13 shown in FIGS. 20 and 21. Besides, because of the flat lens, the fingerprint ridgelines contact the lens 100% and the thickness of the lens can be set at 10 to 20 µm, so that the flat micro-lens sufficiently serves as a protection film.

Figure 23:
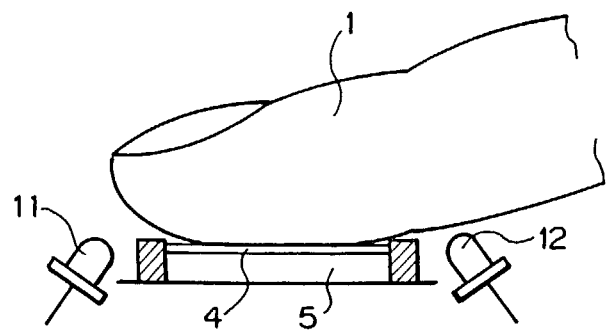
FIG. 23 is a fragmentary sectional view showing the structure of a fingerprint input device which includes two point light sources according to an embodiment of the present invention.
Figure 24A:
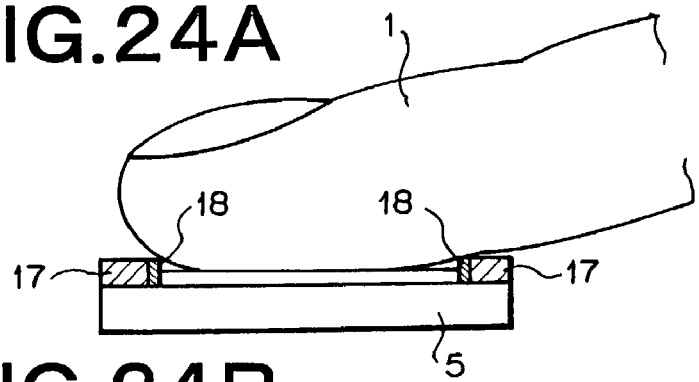
FIG. 24A shows a fragmentary sectional view of the structure of a fingerprint input device which includes a surface light source according to an embodiment of the present invention.
Figure 24B:
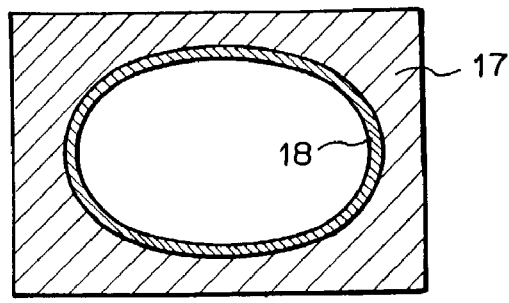
FIG. 24B shows a plan view of the structure of a fingerprint input device which includes a surface light source according to an embodiment of the present invention.

In the meantime, the important requirement of a light source which forms transmission light is to uniformly distribute the light which exits the measured portion of the finger and is originated from the transmission light. To satisfy the requirement, it is preferable that light is applied to the finger from all directions. If the light source is a point light source and strong light is applied to the finger from an opposite surface (a surface on which a claw is present) to the surface of the finger on which the fingerprint measured portion is present, then the uniform distribution of the outgoing light can be obtained. Nevertheless, if the possible fields of application of the fingerprint input devices in the future are considered, it is important to constitute a fingerprint input device to be flat as a whole and light cannot be, therefore, applied to the finger from the surface on which the claw is present. As shown in FIG. 23, it is the best to arrange light sources 11 and 12 on the lower portion of the tip end of the fingertip and that of the first joint of the finger, respectively, if the point light sources are used. However, a method of applying light to the entire finger and making the intensity of light more uniform is realized by using a surface light source 17 shown in FIGS. 24A and 24B and optimizing the shape of the surface light source in accordance with a purpose. In FIGS. 24A and 24B, reference numeral 18 denotes a shielding body which shields the light which otherwise directly enters the photosensitive portion of the sensor from the light source. As the surface light source, a recently developed film-shaped EL light emission panel is appropriate.

Figure 25A:
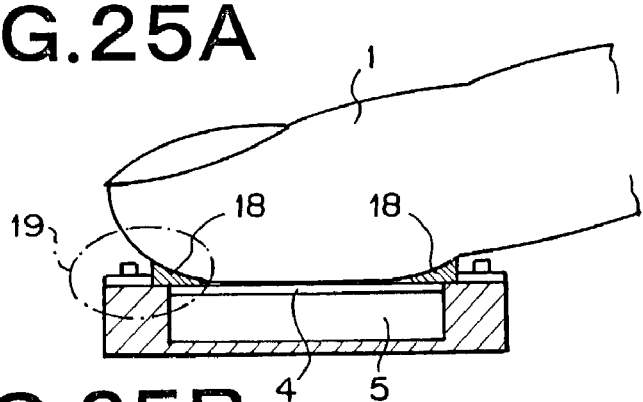
FIG. 25A shows a fragmentary sectional view of the structure of a fingerprint input device which includes a line light source according to an embodiment of the present invention.
Figure 25B:
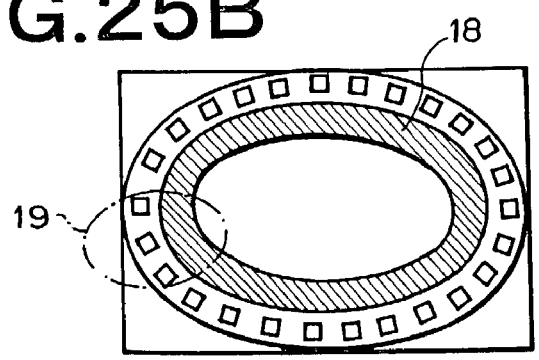
FIG. 25B shows a plan view of the structure of a fingerprint input device which includes a line light source according to an embodiment of the present invention.

A fingerprint input device shown in FIGS. 25A and 25B is designed to further enhance the intensity of light from a measured portion and to optimally arrange light emission diode array chips so as to make outgoing light uniform. In FIGS. 25A and 25B, reference numeral 18 denotes a shielding body which shields light which otherwise directly enters a photosensitive portion from a light source, and 19 denotes a line light emission module (LED chip array). The fingerprint input device shown in FIGS. 25A and 25B is capable of freely designing light amount. The light quantity is designed so as to find the optimal arrangement of the line light emission module to minimize the irregularity of the light emitted from the finger.

FIGS. 12A and 12B show an example of a prototype of the fingerprint input device of the type shown in FIGS. 25A and 25B. In FIGS. 12A and 12B, reference numeral 4 denotes a transparent solid film, 5 denotes a two-dimensional image sensor, 8 denotes a sensor cover, 18 denotes a shielding body which shields light which otherwise directly enters a photosensitive portion from a light source, 19 denotes a line light emission module (LED chip array), 24 denotes an LED chip, 25 denotes a main substrate, and 26 denotes the substrate of the LED array. The most notable feature of this prototype is in that the line light emission module 19 is thin and the thickness of the fingerprint input device shown in FIGS. 25A and 25B can be, therefore, set almost equal to that of the two-dimensional image sensor 5.

Embodiment 4

Figure 26:
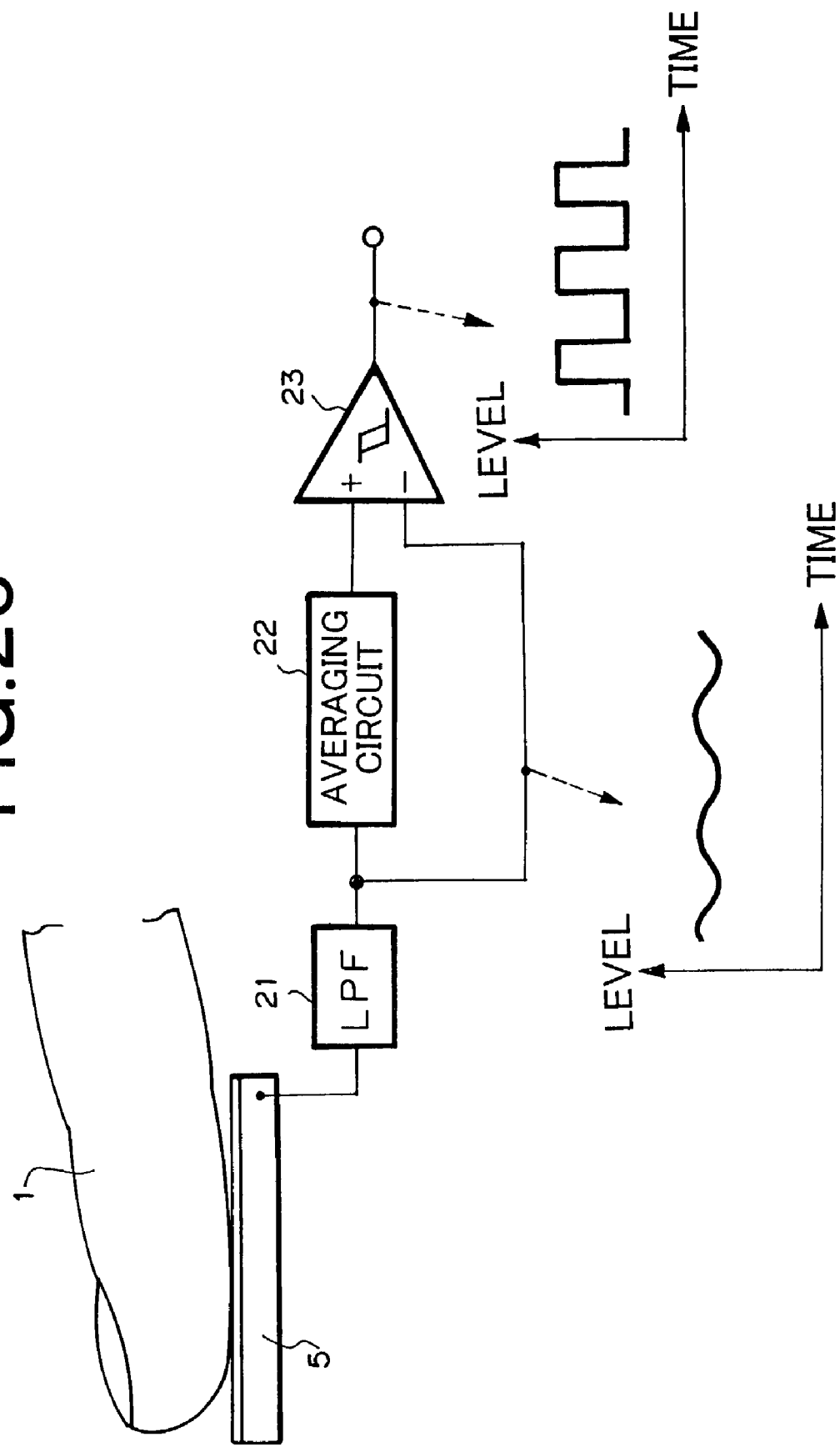
FIG. 26 is a block diagram showing the configuration of a pulsation detection circuit according to Embodiment 4 of the present invention.

In Embodiment 4, the phenomenon that transmission light fluctuates according to the pulsating flow of blood is used and it is discriminated whether or not a fingerprint is a fingerprint of a living body according to the feature of this pulsating flow during measurement so as to prevent illegal use by a fabricated finger. FIG. 26 is a block diagram showing a pulsation detection circuit in Embodiment 4. The pulsation detection circuit operates as follows. An infrared ray is used as measurement light having a wavelength of 800 to 950 nm and a spectrometric filter having a transmission wavelength equal to the wavelength of the infrared ray. In this waveband, the blood (artery) containing much oxygen and the blood (vein) containing less oxygen hardly differ in absorption coefficient from each other and the amount of transmitted light has a fluctuation of about 10%. The peak of the output waveform of a two-dimensional image sensor has change, though 10% or less, according to the change of the light absorption quantity of the blood. This is due to the pulsation of blood pressure. A low-pass filter circuit (LPF) 21 obtains the average lightness of one frame, an averaging circuit 22 averages the average lightness of frames over time longer than a pulse cycle, and a Schmidt comparator 23 compares the output of the low-pass filter circuit 21 with that of the averaging circuit 22, whereby it is possible to detect whether or not there is a pulsation. If there is a pulsation, the output of the comparator 23 has a rectangle waveform. If there is not a pulsation, the output of the comparator 23 remains constant. Therefore, it is possible to discriminate the finger of a human body from a fabricated finger. It is also possible to realize the functions of the low-pass filter circuit 21, the averaging circuit 22 and the comparator 23 by a computer which digitizes the output of the two-image sensor and operates according to a program.

The basic advantages of the present invention are in that the fingerprint input device itself can be made as thin as a two-dimensional sensor chip and in that manufacturing cost is very low because of no use of a fiber flux or the like. The advantages can satisfy the most significant factor of various types of portable information terminals for individual authentication. Besides, the present invention is suited for various usages including cards, the security related to auto vehicles and the like. The advantages of the present invention are concretely described as follows.

Since the fingerprint input device of the present invention is an optical system, static electricity does not influence image formation, i.e., electrical characteristic.

Because the fingerprint input device according to the present invention is especially of direct type among optical fingerprint input devices, no prism, lens and the like are necessary and there is no portion generating an optical distortion, whereby an accurate image can be obtained. Further, the input device of the present invention can be made as thin and small in size as an LSI chip for an image sensor because there is no optical system such as a prism and a lens which requires a space.

Because the fingerprint input device according to the present invention is especially of transmission type among direct types of optical fingerprint input device, disturbance light does not adversely influence the fingerprint input device in the optical system as compared with a light reflection type fingerprint input device and the structure of the device is simple. In addition, since it is unnecessary to apply light to a measured surface unlike the reflection type input device, it is possible to densely arrange sensor elements and to ensure high resolution.

Since it is unnecessary to use an optical fiber flux despite the light transmission type input device, the thickness of the fingerprint measured portion is almost the same as that of the chip of the two-dimensional image sensor.

Since it is unnecessary to use an expensive optical fiber and the structure of the input device is simple, manufacturing cost is low.

Even if a transparent solid film is interposed between the two-dimensional image sensor and the fingerprint measured portion, the clearness of a fingerprint image does not deteriorate unless the transparent solid film has a thickness not less than a predetermined thickness. Therefore, by selecting a hard material such as a vitreous material, the fingerprint input device can be used even in a bad environment such as outdoors.

If the fingerprint input device is used in an environment in which disturbance light tends to enter the fingerprint measured portion, a near-infrared light source and a corresponding filter are employed, thereby making it possible to obtain a stable fingerprint image.

By selecting an optimal light source from those of the present invention, it is possible to make the light amount of the entire measured surface uniform and to almost dispense with the correction of the image by a signal processing.

The LED module among the optimal light sources is capable of designing an optimal light distribution according to the usage. It is, therefore, possible to obtain further uniform image.

The fingerprint sensor system of the present invention is capable of discriminating a fingerprint image of the fingerprint of a living body from a fingerprint image of a fabricated fingerprint.

If a fingerprint sensor with micro-lenses is employed, a less amount of input light and lower power for the light source are required.

What is claimed is:

1. A fingerprint input device comprising:
   at least one light source injecting light into a cortex of a measurement target finger, said light scattering inside said measurement target finger;
   a two-dimensional image sensor for picking up a fingerprint image from a fingerprint measured portion of the measurement target finger, said fingerprint measured portion having a fingerprint ridgeline portion and a fingerprint valley portion, said fingerprint image being formed upon a surface of said two-dimensional image sensor by an incident light from said inside of said measurement target finger that is incident upon the surface of said two-dimensional image sensor; and
   a transparent solid film mounted on an image pickup surface of said two-dimensional image sensor, said fingerprint measured portion being mounted on said transparent solid film when said two-dimensional image sensor picks up said fingerprint image,
   wherein said fingerprint input device picks up an image of said fingerprint ridgeline portion in said fingerprint measured portion as a light portion, and picks up an image of said fingerprint valley portion in said fingerprint measured portion as a dark portion, based on a difference of light direction in said fingerprint valley portions due to differences of refractive indices at an air interface in said valley portion.

2. The fingerprint input device according to claim 1, wherein said refractive index of said transparent solid film is about 1.4 or more.

3. The fingerprint input device according to claim 1, wherein said refractive index of said transparent solid film is about 5 or less.

4. The fingerprint input device according to claim 3, wherein said refractive index of said transparent solid film is about 4 or less.

5. The fingerprint input device according to claim 4, wherein said refractive index of said transparent solid film is about 3 or less.

6. The fingerprint input device according to claim 5, wherein said refractive index of said transparent solid film is about 2 or less.

7. The fingerprint input device according to claim 1, wherein a thickness of said transparent solid film is about 100 μm or less and more than about 0 μm.

8. The fingerprint input device according to claim 7, wherein said thickness of said transparent solid film is about 90 μm or less.

9. The fingerprint input device according to claim 8, wherein said thickness of said transparent solid film is about 80 μm or less.

10. The fingerprint input device according to claim 9, wherein said thickness of said transparent solid film is about 70 μm or less.

11. The fingerprint input device according to claim 10, wherein said thickness of said transparent solid film is about 60 μm or less.

12. A fingerprint input device comprising:
    a two-dimensional image sensor for picking up a fingerprint image from a fingerprint measured portion of a measurement target finger, said fingerprint measured portion having a fingerprint ridgeline portion and a fingerprint valley portion; and
    a transparent solid film mounted on an image pickup surface of said two-dimensional image sensor, said fingerprint measured portion being mounted on said transparent solid film when said two-dimensional image sensor picks up said fingerprint image,
    wherein said fingerprint input device picks up an image of the fingerprint ridgeline portion in said fingerprint measured portion as a light portion, and picks up an image of the fingerprint valley portion in said fingerprint measured portion as a dark portion,
    wherein a refractive index $n_3$ of said transparent solid film satisfies a condition that contrast $C_0$ is equal to or more than a value for obtaining a signal to noise ratio for fingerprint recognition when a magnitude of noise is given, said contrast $C_0$ being defined for a case where a thickness of said transparent solid film is as close as zero, and being obtained by assigning equations 2 and 3 to an equation 1 under a first condition that a refractive index $n_3$ of said transparent solid film<a refractive index $n_1$ of a cortex of said finger>a refractive index $n_2=1.000$ of air and being obtained by assigning equations 2 and 4 to the equation 1 under a second condition that the refractive index $n_1$ of the cortex of said finger>the refractive index $n_3$ of said transparent solid film<the refractive index $n_2=1.000$ of the air, wherein said equation 1 is as follows:

$$C_0 = (P_{3L} - P_{3D})/P_{3L}$$

where
- $P_{3L}$: power of downward light in all directions right under the fingerprint valley portion, and
- $P_{3D}$: the power of the downward light in all directions right under the fingerprint ridgeline portion, wherein said equation 2 is as follows:

$$C_0 = (P_{3L} - P_{3D})/P_{3L}$$

where
- $P_{3L}$: power of downward light in all directions right under the fingerprint valley portion, and
- $P_{3D}$: the power of the downward light in all directions right under the fingerprint ridgeline portion, wherein said equation 2 is as follows:

$$P_{3D} = \left(|p_1| \cdot \int_0^{\theta_C(1)} t_D() d\theta_{1D}\right) \cdot \left(\int_0^{90°} t_D() d\theta_{2Di}\right)$$

$$\theta_{C(\text{①} \to \text{②})} = \sin^{-1}(n_2/n_1)$$

$$t_{D(\text{①} \to \text{②})} = (1/2) \cdot (\sin 2\theta_{1D} \cdot \sin 2\theta_{2D})/\sin^2(\theta_{1D}+\theta_{2D}) \cdot (1+1/\cos(\theta_{1D}-\theta_{2D}))$$

$$\theta_{2D} = \sin^{-1}(n_1/n_2 \sin \theta_{1D})$$

$$t_{D(\text{②} \to \text{③})} = (1/2) \cdot (\sin 2\theta_{2Di} \cdot \sin 2\theta_{3D})/\sin^2(\theta_{2Di}+\theta_{3D}) \cdot (1+1/\cos(\theta_{2Di}-\theta_{3D}))$$

$$\theta_{3D} = \sin^{-1}(n_2/n_3 \sin \theta_{2Di})$$

- $\theta_{1D}$: the incidence angle of light incident on the air layer in the fingerprint valley portion
- $\theta_{2Di}$: the incidence angle of light incident on the transparent solid film from the air layer right under the fingerprint valley portion wherein said equation 3 is as follows:

$$P_{3L} = \left(|p_1| \cdot \int_0^{90°} t_L() d\theta_{1D}\right)$$

where $$t_{D(\text{①} \to \text{③})} = (1/2) \cdot (\sin 2\theta_{1L} \cdot \sin 2\theta_{3L})/\sin^2(\theta_{1L}+\theta_{3L}) \cdot (1+1/\cos(\theta_{1L}-\theta_{3L}))$$

$$\theta_{3L} = \sin^{-1}(n_1/n_3 \sin \theta_{1L})$$

- $\theta_{1L}$: the incidence angle of light incident on the transparent solid film from the fingerprint ridgeline portion and wherein said equation 4 is as follows:

$$P_{3L} = \left(|p_1| + \int_0^{\theta_C()} t_L() d\theta_{1D}\right)$$

where $$\theta_{C(\text{①} \to \text{③})} = \sin^{-1}(n_3/n_1)$$

$$t_{D(\text{①} \to \text{③})} = (1/2) \cdot (\sin 2\theta_{1L} \cdot \sin 2\theta_{3L})/\sin^2(\theta_{1L}+\theta_{3L})/\sin^2(\theta_{1L}-\theta_{3L}))$$

$$\theta_{3L} = \sin^{-1}(n_1/n_3 \sin \theta_{1L})$$

13. The fingerprint input device according to claim 12, wherein a thickness t of said transparent solid film satisfies a condition that a value of contrast $C_1$ defined for the thickness t of said transparent solid film is equal to or more than a value for obtaining a signal to noise ratio for fingerprint recognition when a magnitude of noise is given, said contrast $C_1$ being expressed by an equation as follows:

$$C_1 = 1 - \frac{(1-C_0)\tan^{-1}\frac{1-\gamma}{2\beta} + \tan^{-1}\frac{1}{2\beta} - \tan^{-1}\frac{\gamma}{2\beta}}{\tan^{-1}\frac{\gamma}{2\beta} + (1-C_0)\tan^{-1}\frac{1}{2\beta} - (1-C_0)\tan^{-1}\frac{\gamma}{2\beta}}$$

where $\beta = t/w$,
- w: a distance between fingerprint ridgelines, and
- $\gamma$: a duty of the fingerprint ridgeline portion.

14. The fingerprint input device according to claim 1 or 12, wherein said transparent solid film comprises glass as a composition.

15. The fingerprint input device according to claim 1 or 12, wherein a composition of said transparent solid film has a flexibility.

16. The fingerprint input device according to claim 15, wherein said composition having said flexibility comprises polyimide or polycarbonate.

17. The fingerprint input device according to claims 1 or 12, further comprising a grounded, electrical conductive transparent film.

18. The fingerprint input device according to claim 17, wherein said conductive transparent film comprises tin oxide or indium-tin-oxide as a composition.

19. The fingerprint input device according to claim 17, wherein said electrical conductive transparent film is an uppermost layer.

20. The fingerprint input device according to claim 1 or 12, wherein said at least one light source irradiates light to a portion closer to a fingertip than a first joint of said measurement target finger from a surface different from said fingerprint measured portion.

21. The fingerprint input device according to claim 20, wherein said at least one light source comprises:
- a first light source irradiating the light to the fingertip of said measurement target finger; and
- a second light source irradiating the light to said first joint of said measurement target finger.

22. The fingerprint input device according to claim 20, wherein said at least one light source comprises a surface light source applying the light to an outer peripheral portion of the fingerprint measured portion of said measurement target finger.

23. The fingerprint input device according to claim 20, wherein said at least one light source comprises a line light source applying the light to an outer peripheral portion of the fingerprint measured portion of said measurement target finger.

24. The fingerprint input device according to claim 20, wherein said at least one light source emits only light in a predetermined waveband.

25. The fingerprint input device according to claim 24, wherein a spectroscopic filter passing only the light in said predetermined waveband is located at any position between said two-dimensional image sensor and a surface of the fingerprint input device.

26. The fingerprint input device according to claim 24, wherein said transparent solid film is transparent only for said predetermined waveband.

27. The fingerprint input device according to claim 24, wherein said predetermined waveband is in a range from about 800 to about 950 nm.

28. The fingerprint input device according to claim 1 or 12, wherein said transparent solid film is partitioned by a light shielding wall formed by perforating many penetrating holes in a film made of a light shielding material.

29. The fingerprint input device according to claim 28, wherein a diameter of each of said penetrating holes is equal to or less than a half a light receiving diameter of a light receiving of said two-dimensional image sensor.

30. The fingerprint input device according to claim 28, wherein said penetrating holes are aligned to light receiving elements of said two-dimensional image sensor.

31. The fingerprint input device according to claim 28, wherein said light shielding material is electrically conductive and grounded.

32. The fingerprint input device according to claim 1 or 12, further comprising a plurality of micro-lenses laminated with said transparent solid film and mounted on respective light receiving elements on the image pickup surface of said two-dimensional image sensor,
wherein a refractive index of each of said plurality of micro-lenses is higher than the refractive index of said transparent solid film.

33. The fingerprint input device according to claim 1 or 12, further comprising a plurality of micro-lenses formed on said transparent solid film and mounted on respective light receiving elements on the image pickup surface of said two-dimensional sensor, wherein a refractive index of each of said plurality of micro-lenses is higher than the refractive index of said transparent solid film.

34. The fingerprint input device according to claim 33, wherein the refractive index of each of said plurality of micro-lenses changes along a distance from said light receiving element.

35. The fingerprint input device according to claim 1 or 12, further comprising means for detecting whether or not there is a pulsation at the measurement target finger.

36. A fingerprint input device comprising:
a two-dimensional image sensor for picking up a fingerprint image of a fingerprint in a fingerprint measured portion of a measurement target finger, said fingerprint image being formed on a surface of said two-dimensional image sensor by an incident light that is incident upon said surface of said two-dimensional image sensor from an inside of said measurement target finger, said fingerprint image resulting from a difference in refraction due to said light from inside said measurement target finger passing through air; and
a plurality of micro-lenses mounted on respective light receiving elements on an image pickup surface of said two-dimensional image sensor, said fingerprint measured portion being mounted on said plurality of micro-lenses when said two-dimensional image sensor picks up said fingerprint image,
wherein said fingerprint input device picks up an image of a fingerprint ridgeline portion in said fingerprint measured portion as a light portion, and picks up an image of a fingerprint valley portion in said fingerprint measured portion as a dark portion,
wherein a refractive index of each of said plurality of micro-lenses is 1.4 or more.

37. The fingerprint input device according to claim 36, wherein said refractive index of said transparent solid film is about 1.5 or more.

38. The fingerprint input device according to claim 36, wherein said refractive index of said transparent solid film is about 5 or less.

39. The fingerprint input device according to claim 38, wherein said refractive index of said transparent solid film is about 4 or less.

40. The fingerprint input device according to claim 39, wherein said refractive index of said transparent solid film is about 3 or less.

41. The fingerprint input device according to claim 40, wherein said refractive index of said transparent solid film is about 2 or less.

42. A fingerprint input device comprising:
a two-dimensional image sensor for picking up a fingerprint image of a fingerprint in a fingerprint measured portion of a measurement target finger; and
a plurality of micro-lenses mounted on respective light receiving elements on an image pickup surface of said two-dimensional image sensor, said fingerprint measured portion being mounted on said plurality of micro-lenses when said two-dimensional image sensor picks up said fingerprint image,
wherein said fingerprint input device picks up an image of a fingerprint ridgeline portion in said fingerprint measured portion as a light portion, and picks up an image of a fingerprint valley portion in said fingerprint measured portion as a dark portion, and
wherein a refractive index $n_3$ of said micro-lenses satisfies a condition that contrast $C_0$ is equal to or more than a value for obtaining a signal to noise ratio for fingerprint recognition when a magnitude of noise is given, said contrast $C_0$ being defined for a case where a thickness of said micro-lenses is as close as zero, and being obtained by assigning equations 2 and 3 to an equation 1 under a first condition that a refractive index $n_3$ of said micro-lenses>a refractive index $n_1$ of a cortex of said finger>a refractive index $n_2$=1.000 of air and being obtained by assigning equations 2 and 3 to the equation 1 under a second condition that the refractive index $n_1$ of the cortex of said finger>the refractive index $n_3$ of said micro-lenses> the refractive index $n_2$=1.000 of the air,
wherein said equation 1 is as follows:

$C_0 = (P_{3L} - P_{3D})/P_{3L}$ where
$P_{3L}$: power of downward light in all directions right under the fingerprint valley portion, and
$P_{3D}$: the power of the downward light in all directions right under the fingerprint ridgeline portion,
wherein said equation 2 is as follows:

$$P_{3D} = \left(|p_1| \cdot \int_0^{\theta_{C()}} t_D() d\theta_{1D}\right) \cdot \left(\int_0^{90°} t_D() d\theta_{2Di}\right)$$

where $\theta_{C(①\to②)} = \sin^{-1}(n_2/n_1)$ $t_{D(①\to②)} = (\frac{1}{2}) \cdot (\sin 2\theta_{1D} \cdot \sin 2\theta_{2D})/\sin^2(\theta_{1D}+\theta_{2D}) \cdot (1+1/\cos(\theta_{1D}-\theta_{2D}))$ $\theta_{2D} = \sin^{-1}(n_1/n_2 \sin \theta_{1D})$ $t_{D(②\to③)} = (\frac{1}{2}) \cdot (\sin 2\theta_{2Di} \cdot \sin 2\theta_{3D})/\sin^2(\theta_{2Di}+\theta_{3D}) \cdot (1+1/\cos(\theta_{2Di}-\theta_{3D}))$ $\theta_{3D} = \sin^{-1}(n_2/n_3 \sin \theta_{2Di})$ $\theta_{1D}$: the incidence angle of light incident on the air layer in the fingerprint valley portion $\theta_{2Di}$: the incidence angle of light incident on the transparent solid film from the air layer right under the fingerprint valley portion wherein said equation 3 is as follows:

$$P_{3L} = \left( |p_1| \cdot \int_0^{90°} t_L() d\theta_{1D} \right)$$

where $t_{D(\text{①} \to \text{③})} = (\frac{1}{2}) \cdot (\sin 2\theta_{1L} \cdot \sin 2\theta_{3L}) / \sin^2(\theta_{1L}+\theta_{3L}) \cdot (1+ 1/\cos(\theta_{1L}-\theta_{3L}))$ $\theta_{3L} = \sin^{-1}(n_1/n_3 \sin \theta_{1L})$ $\theta_{1L}$: the incidence angle of light incident on the transparent solid film from the fingerprint ridgeline portion and wherein said equation 4 is as follows:

$$P_{3L} = \left( |p_1| + \int_0^{\theta_c()} t_L() d\theta_{1D} \right)$$

where $\theta_{C(\text{①} \to \text{③})} = \sin^{-1}(n_3/n_1)$ $t_{D(\text{①} \to \text{③})} = (\frac{1}{2}) \cdot (\sin 2\theta_{1L} \cdot \sin 2\theta_{3L}) / \sin^2(\theta_{1L}+\theta_{3L}) / \sin^2(\theta_{1L}-\theta_{3L})$ $\theta_{3L} = \sin^{-1}(n_1/n_3 \sin \theta_{1L})$.

* * * * *